US009175352B2

(12) United States Patent
Keutgen et al.

(10) Patent No.: US 9,175,352 B2
(45) Date of Patent: Nov. 3, 2015

(54) DISTINGUISHING BENIGN AND MALIGNANT INDETERMINATE THYROID LESIONS

(71) Applicant: Cornell University, Ithaca, NY (US)

(72) Inventors: Xavier M. Keutgen, New York, NY (US); Thomas J. Fahey, III, Larchmont, NY (US); Olivier Elemento, New York, NY (US); Rasa Zarnegar, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/586,115

(22) Filed: Dec. 30, 2014

(65) Prior Publication Data

US 2015/0125387 A1    May 7, 2015

Related U.S. Application Data

(60) Division of application No. 14/032,785, filed on Sep. 20, 2013, now Pat. No. 8,945,829, which is a continuation of application No. PCT/US2012/030077, filed on Mar. 22, 2012.

(60) Provisional application No. 61/466,395, filed on Mar. 22, 2011, provisional application No. 61/598,172, filed on Feb. 13, 2012.

(51) Int. Cl.
| | |
|---|---|
| *A61K 48/00* | (2006.01) |
| *C12N 15/113* | (2010.01) |
| *C07H 21/04* | (2006.01) |
| *C07H 21/02* | (2006.01) |
| *C12Q 1/68* | (2006.01) |
| *G06F 19/20* | (2011.01) |

(52) U.S. Cl.
CPC ........ *C12Q 1/6886* (2013.01); *C12Q 2600/112* (2013.01); *C12Q 2600/158* (2013.01); *C12Q 2600/178* (2013.01); *G06F 19/20* (2013.01)

(58) Field of Classification Search
CPC .............................. A61K 48/00; C12N 15/113
See application file for complete search history.

(56) References Cited

U.S. PATENT DOCUMENTS

| | | | |
|---|---|---|---|
| 8,465,914 | B2 | 6/2013 | Brown et al. |
| 8,945,829 | B2 | 2/2015 | Keutgen et al. |
| 2009/0123912 | A1 | 5/2009 | Raymond |
| 2010/0203544 | A1 | 8/2010 | Croce et al. |
| 2011/0014603 | A1 | 1/2011 | Eng et al. |
| 2011/0112173 | A1 | 5/2011 | Brown et al. |
| 2011/0152357 | A1 | 6/2011 | Croce |
| 2011/0160290 | A1 | 6/2011 | Tewari |
| 2011/0312520 | A1 | 12/2011 | Kennedy et al. |
| 2012/0264631 | A1 | 10/2012 | Eng et al. |
| 2013/0017972 | A1 | 1/2013 | Brown et al. |
| 2014/0099261 | A1 | 4/2014 | Keutgen et al. |

FOREIGN PATENT DOCUMENTS

| | | |
|---|---|---|
| CA | 2572450 A1 | 12/2005 |
| WO | WO-2005078139 A2 | 8/2005 |
| WO | WO-2008002672 A2 | 1/2008 |
| WO | WO-2008073920 A2 | 6/2008 |
| WO | WO-2010056374 A2 | 5/2010 |
| WO | WO-2010115833 A1 | 10/2010 |
| WO | WO-2010129934 A2 | 11/2010 |
| WO | WO-2011137288 A2 | 11/2011 |
| WO | WO-2011143361 A2 | 11/2011 |
| WO | WO-2012009499 A2 | 1/2012 |
| WO | WO-2012012051 A2 | 1/2012 |
| WO | WO-2012129378 A1 | 9/2012 |

OTHER PUBLICATIONS

"European Application Serial No. 12760780.2, Extended European Search Report mailed Nov. 21, 2014", 12 pgs.
Kutgen, X M, et al., "Measurement of Four MicroRNAs Accurately Differentiates Malignant from Benign Indeterminate Thyroid Lesions", Clinical Thyroidology 24,(5), (2012), 7-8.
Marini, Francesca, et al., "MicroRNA Role in Thyroid Cancer Development", Journal of Thyroid Research, vol. 2011, No. 28,, (2011), 1-12.
"U.S. Appl. No. 14/032,785, Non Final Office Action mailed Apr. 30, 2014", 12 pgs.
"U.S. Appl. No. 14/032,785, Notice of Allowance mailed Sep. 22, 2014", 8 pgs.
"U.S. Appl. No. 14/032,785, Reponse filed Apr. 8, 2014 to Restriction Requirement mailed Mar. 6, 2014", 9 pgs.
"U.S. Appl. No. 14/032,785, Response filed Jul. 30, 2014 to Non Final Office Action mailed Apr. 30, 2014", 11 pgs.
"U.S. Appl. No. 14/032,785, Restriction Requirement mailed Mar. 6, 2014", 9 pgs.
"International Application Serial No. PCT/US2012/030077, International Preliminary Report on Patentability mailed Oct. 3, 2013", 10 pgs.
"International Application Serial No. PCT/US2012/030077, International Search Report mailed Jun. 29, 2012", 2 pgs.
"International Application Serial No. PCT/US2012/030077, Written Opinion mailed Jun. 29, 2012", 8 pgs.
Brown, M. P. S., et al., "Knowledge-based analysis of microarray gene expression data by using support vector machines", Proc. Natl. Acad. Sci. USA, 97(1), (2000), 262-267.
Calin, G. A., et al., "Frequent deletions and down-regulation of micro-RNA genes miR15 and miR16 at 13q14 in chronic lymphocytic leukemia", Proc. Natl. Acad. Sci. USA, 99(24), (2002), 15524-15529.
Chan, J. A., et al., "MicroRNA-21 Is an Antiapoptotic Factor in Human Glioblastoma Cells", Cancer Research, 65, (2005), 6029-6033.
Chen, Y.-T., et al., "MicroRNA analysis as a potential diagnostic tool for papillary thyroid carcinoma", Modern Pathology, 21, (2008), 1139-1146.

(Continued)

*Primary Examiner* — Amy Bowman
(74) *Attorney, Agent, or Firm* — Schwegman Lundberg & Woessner, P.A.

(57) ABSTRACT

The application describes methods for accurately evaluating whether thyroid test samples, especially indeterminate thyroid samples, are benign or malignant.

12 Claims, 2 Drawing Sheets

(56) References Cited

OTHER PUBLICATIONS

Cheng, A. M., et al., "Antisense inhibition of human miRNAs and indications for an involvement of miRNA in cell growth and apoptosis", Nucleic Acids Research, 33(4), (2005), 1290-1297.

He, H., et al., "The role of microRNA genes in papillary thyroid carcinoma", Proc. Natl. Acad. Sci. USA, 102(52), (2005), 19075-19080.

Iorio, M. V., et al., "MicroRNA Gene Expression Deregulation in Human Breast Cancer", Cancer Research, 65(16), (2005), 7065-7070.

Keutgen, X. M., et al., "A Panel of Four mRNAs Accurately Differentiates Malignant from Benign Indeterminate Thyroid Lesions on Fine Needle Aspiration", Clin. Cancer Res., 18(7), (2012), 2032-2038.

Lagos—Quintana, M., et al., "New microRNAs from mouse and human", RNA, 9, (2003), 175-179.

Liu, C.-G., et al., "An oligonucleotide microchip for genome-wide microRNA profiling in human and mouse tissues", Proc. Natl. Acad. Sci. USA, 101(26), (2004), 9740-9744.

McManus, M. T., "MicroRNAs and cancer", Seminars in Cancer Biology, 13, (2003), 253-258.

Menon, M. P., et al., "Micro-RNAs in thyroid neoplasms: molecular, diagnostic and therapeutic implications", J. Clin. Pathol., 62, (2009), 978-985.

Nikiforova, M. N., et al., "MicroRNA Expression Profiling of Thyroid Tumors: Biological Significance and Diagnostic Utility", J. Clin. Endocrinol. Metab., 93(5), (2008), 1600-1608.

Nikiforova, M. N., et al., "Molecular Diagnostics and Predictors in Thyroid Cancer", Thyroid, 19(12), (2009), 1351-1361.

Pallante, P., et al., "Deregulation of microRNA expression in follicular cell-derived human thyroid carcinomas", Endocrine-Related Cancer, 17, (2010), F91-F104.

Pallante, P., et al., "MicroRNA deregulation in human thyroid papillary carcinomas", Endocrine-Related Cancer, 13, (2006), 497-508.

Poliseno, et al., "MicroRNAs modulate the angiogenic properties of HUVECs", Blood, 108(9), (2006), 3068-3071.

Sheu, S.-Y., et al., "Differential miRNA expression profiles in variants of papillary thyroid carcinoma and encapsulated follicular thyroid tumours", British Journal of Cancer, 102(2), (2010), 376-382.

Visone, R., et al., "MicroRNAs (miR)-221 and miR-222, both overexpressed in human thyroid papillary carcinomas, regulate p27Kip1 protein levels and cell cycle", Endocr. Relat. Cancer, 14, (2007), 791-798.

Visone, R., et al., "Specific microRNAs are downregulated in human thyroid anaplastic carcinomas", Oncogene, 26, (2007), 7590-7595.

Wang, C.-H., et al., "MicroRNA miR-328 Regulates Zonation Morphogenesis by Targeting CD44 Expression", PLoS ONE, 3(6): e2420, (2008), 1-14.

Weber, F., et al., "A Limited Set of Human MicroRNA Is Deregulated in Follicular Thyroid Carcinoma", The Journal of Clinical Endocrinology & Metabolism, 91(9), (2006), 3584-3591.

Wiemer, E. A. C., "The role of microRNAs in cancer: No small matter", European Journal of Cancer, 43, (2007), 1529-1544.

SEQUENCE LISTING

<160> NUMBER OF SEQ ID NOS: 24

<210> SEQ ID NO 1
<211> LENGTH: 75
<212> TYPE: DNA
<213> ORGANISM: Homo sapiens

<400> SEQUENCE: 1
tggagtgggg gggcaggagg ggctcaggga gaaagtgcat acagccctg gccctctctg    60 cccttccgtc ccctg    75

<210> SEQ ID NO 2
<211> LENGTH: 75
<212> TYPE: RNA
<213> ORGANISM: Homo sapiens

<400> SEQUENCE: 2
uggagugggg gggcaggagg ggcucaggga gaaagugcau acagcccug gcccucucug    60 cccuuccguc cccug    75

<210> SEQ ID NO 3
<211> LENGTH: 23
<212> TYPE: RNA
<213> ORGANISM: Homo sapiens

<400> SEQUENCE: 3
ccuggcccuc ucugcccuuc cgu    23

<210> SEQ ID NO 4
<211> LENGTH: 110
<212> TYPE: DNA
<213> ORGANISM: Homo sapiens

<400> SEQUENCE: 4
gctgctggaa ggtgtaggta ccctcaatgg ctcagtagcc agtgtagatc ctgtctttcg    60
taatcagcag ctacatctgg ctactgggtc tctgatggca tcttctagct    110

```
<210> SEQ ID NO 5
<211> LENGTH: 110
<212> TYPE: RNA
<213> ORGANISM: Homo sapiens

<400> SEQUENCE: 5
gcugcuggaa gguguaggua cccucaaugg cucaguagcc aguguagauc cugucuuucg    60
uaaucagcag cuacaucugg cuacuggguc ucugauggca ucuucuagcu              110

<210> SEQ ID NO 6
<211> LENGTH: 21
<212> TYPE: RNA
<213> ORGANISM: Homo sapiens

<400> SEQUENCE: 6
agcuacaucu ggcuacuggg u                                              21

<210> SEQ ID NO 7
<211> LENGTH: 75
<212> TYPE: DNA
<213> ORGANISM: Homo Sapiens

<400> SEQUENCE: 7
ggctgtgccg ggtagagagg gcagtgggag gtaagagctc ttcacccttc accaccttct    60
ccacccagca tggcc                                                     75

<210> SEQ ID NO 8
<211> LENGTH: 75
<212> TYPE: RNA
<213> ORGANISM: Homo sapiens

<400> SEQUENCE: 8
ggcugugccg gguagagagg gcagugggag guaagagcuc uucacccuuc accaccuucu    60
ccacccagca uggcc                                                     75

<210> SEQ ID NO 9
<211> LENGTH: 22
<212> TYPE: RNA
<213> ORGANISM: Homo sapiens

<400> SEQUENCE: 9
uucaccaccu ucuccaccca gc                                             22

<210> SEQ ID NO 10
<211> LENGTH: 72
<212> TYPE: DNA
<213> ORGANISM: Homo sapiens

<400> SEQUENCE: 10
tgtcgggtag cttatcagac tgatgttgac tgttgaatct catggcaaca ccagtcgatg    60
ggctgtctga ca                                                        72

<210> SEQ ID NO 11
<211> LENGTH: 72
<212> TYPE: RNA
<213> ORGANISM: Homo sapiens

<400> SEQUENCE: 11
ugucggguag cuuaucagac ugauguugac uguugaaucu cauggcaaca ccagucgaug    60
ggcugucuga ca                                                        72
```

```
<210> SEQ ID NO 12
<211> LENGTH: 22
<212> TYPE: RNA
<213> ORGANISM: Homo sapiens

<400> SEQUENCE: 12
uagcuuauca gacugauguu ga                                               22

<210> SEQ ID NO 13
<211> LENGTH: 110
<212> TYPE: DNA
<213> ORGANISM: Homo sapiens

<400> SEQUENCE: 13
tgagttttga ggttgcttca gtgaacattc aacgctgtcg gtgagtttgg aattaaaatc      60
aaaaccatcg accgttgatt gtaccctatg ctaaccatc atctactcca                  110

<210> SEQ ID NO 14
<211> LENGTH: 110
<212> TYPE: RNA
<213> ORGANISM: Homo sapiens

<400> SEQUENCE: 14
ugaguuuuga gguugcuuca gugaacauuc aacgcugucg gugaguuugg aauuaaaauc      60
aaaaccaucg accguugauu gtacccuaug cuaaccauc aucuacucca                  110

<210> SEQ ID NO 15
<211> LENGTH: 23
<212> TYPE: RNA
<213> ORGANISM: Homo sapiens

<400> SEQUENCE: 15
aacauucaac gcugucggug agu                                              23

<210> SEQ ID NO 16
<211> LENGTH: 73
<212> TYPE: DNA
<213> ORGANISM: Homo sapiens

<400> SEQUENCE: 16
cctggcactg agaactgaat tccataggct gtgagctcta gcaatgccct gtggactcag      60
ttctggtgcc cgg                                                         73

<210> SEQ ID NO 17
<211> LENGTH: 73
<212> TYPE: RNA
<213> ORGANISM: Homo sapiens

<400> SEQUENCE: 17
ccuggcacug agaacugaau uccauaggcu gugagcucua gcaaugcccu guggacucag      60
uucuggugcc cgg                                                         73

<210> SEQ ID NO 18
<211> LENGTH: 22
<212> TYPE: RNA
<213> ORGANISM: Homo sapiens

<400> SEQUENCE: 18
ugagaacuga auuccauagg cu                                               22
```

```
<210> SEQ ID NO 19
<211> LENGTH: 22
<212> TYPE: RNA
<213> ORGANISM: Homo sapiens

<400> SEQUENCE: 19
uucaccaccu ucuccaccca gc                                              22

<210> SEQ ID NO 20
<211> LENGTH: 22
<212> TYPE: RNA
<213> ORGANISM: Homo sapiens

<400> SEQUENCE: 20
uagcuuauca gacugauguu ga                                              22

<210> SEQ ID NO 21
<211> LENGTH: 24
<212> TYPE: RNA
<213> ORGANISM: Homo sapiens

<400> SEQUENCE: 21
agcuacaucu ggcuacuggg ucuc                                            24

<210> SEQ ID NO 22
<211> LENGTH: 22
<212> TYPE: RNA
<213> ORGANISM: Homo sapiens

<400> SEQUENCE: 22
cuggcccucu cugcccuucc gu                                              22

<210> SEQ ID NO 23
<211> LENGTH: 22
<212> TYPE: RNA
<213> ORGANISM: Homo sapiens

<400> SEQUENCE: 23
ugagaacuga auuccauagg cu                                              22

<210> SEQ ID NO 24
<211> LENGTH: 23
<212> TYPE: RNA
<213> ORGANISM: Homo sapiens

<400> SEQUENCE: 24
aacauucaac gcugucggug agu                                             23
```

DISTINGUISHING BENIGN AND MALIGNANT INDETERMINATE THYROID LESIONS

This application is a divisional of U.S. patent application Ser. No. 14/032,785, filed Sep. 20, 2013, which is a continuation under 35 U.S.C. 111(a) of International Application No. PCT/US2012/030077, filed Mar. 22, 2012 and published as WO 2012/129378 A1 on Sep. 27, 2012, which claims benefit of the filing date of U.S. Provisional Patent Application No. 61/466,395, filed Mar. 22, 2011 and U.S. Provisional Patent Application No. 61/598,172, filed Feb. 13, 2012, the contents of which are specifically incorporated herein in their entirety.

BACKGROUND

Thyroid nodules are very common. The gold standard for assessing thyroid nodules is fine needle aspiration of the nodules with cytopathological evaluation, which yields a diagnosis of benign or malignant lesion in 70% of cases. However, in 30% of cases, cytopathology will not be sufficient to determine the status of these "indeterminate" lesions. Moreover, indeterminate thyroid lesions on Fine Needle Aspiration (FNA) harbor malignancy in about 25% of cases. Hemi-thyroidectomy or total thyroidectomy has been routinely advocated for definitive diagnosis. But when there is no clear diagnosis it is unclear whether such thyroidectomy is appropriate.

In cancer, microRNAs may function as both tumor suppressors and oncogenes. MicroRNAs have also been used for diagnosis of cancer. See, e.g., Wiemer E A. The role of microRNAs in cancer: no small matter. Eur J Cancer 43:1529-44 (2007); Nikiforova et al. Endocr Pathol 20:85-91 (2009); He et al. Proc Natl Acad Sci USA 102:19075-80 (2005); Pallante et al. Endocr Relat Cancer 17:F91-104 (2010); Sheu et al. Br J Cancer 102:376-82 (2010); Chen et al. Mod Pathol 21:1139-46 (2008); Nikiforova et al. J Clin Endocrinol Metab 93:1600-8 (2008); Pallante et al. Endocr Relat Cancer 13:497-508 (2006); Visone et al. Endocr Relat Cancer 14:791-8 (2007); Weber et al. J Clin Endocrinol Metab 91:3584-91 (2006).

However, many different types of microRNAs exist. Scientists have tried without success to discover which set of markers can accurately stage thyroid lesions regarding their malignant potential. In addition, previous studies have not been able to properly assign a malignant/benign status to thyroid lesions defined as indeterminate by cytological analysis.

SUMMARY

This application describes methods for analysis of microRNA expression in indeterminate fine needle aspiration samples and the prognostic value of such methods for determining the malignant or benign status of these samples.

One aspect of the invention is therefore a method of assessing whether a test thyroid tissue sample of indeterminate diagnosis is benign or malignant that involves one or more of the following steps: (a) obtaining or determining a quantified expression level of the following microRNAs: mir-328, mir-222, mir-197, mir-181a, mir-146b and/or mir-21 RNA in the test thyroid tissue sample to obtain a test dataset of expression levels; (b) comparing the test dataset of expression levels to a malignant thyroid dataset and to a benign thyroid dataset; (c) determining whether the test dataset of expression levels is statistically significantly within the malignant thyroid dataset or within the benign thyroid dataset to thereby assess whether the test thyroid tissue sample is benign or malignant; wherein the malignant thyroid dataset is a collection of quantified expression levels of mir-328, mir-222, mir-197, mir-181a, mir-146b and/or mir-21 RNA from malignant thyroid tissue samples; and wherein the benign thyroid dataset is a collection of quantified expression levels mir-328, mir-222, mir-197, mir-181a, mir-146b and/or mir-21 RNAs from benign, healthy, and/or non-cancerous thyroid tissue samples. In some embodiments the test, malignant and benign datasets are quantified expression level of the following microRNAs: mir-328, mir-222, mir-197, and mir-21 RNAs.

Another aspect of the invention is a method for constructing a malignant/benign discrimination process for assessing test thyroid tissue samples that includes one or more of the following steps: (a) obtaining a 'malignant' dataset of quantified miRNA expression levels in tissue samples from patients having malignant thyroid cancer; (b) obtaining a 'benign' dataset of quantified miRNA expression levels in tissue samples from patients having benign thyroid cancer; and (c) training a benign/malignancy predictor, wherein the benign/malignancy predictor receives input that includes the malignant dataset and the benign dataset and generates a multi-dimensional map distinguishing the malignant dataset from the benign dataset. The method can also include another step (d) involving repeating steps (a)-(c) for a plurality of iterations as data on at least one new quantified miRNA expression level is added to the malignant dataset or the benign dataset. This method can also include another step (e) that includes comparing test result data comprising quantified miRNA expression level(s) of a test thyroid tissue sample with the malignant dataset and the benign dataset to predict whether the test thyroid tissue sample is malignant or benign. The quantified miRNA expression levels in the malignant dataset, the benign dataset and the test result data of a test thyroid tissue sample can be expression levels of the following microRNAs: mir-328, mir-222, mir-197, mir-181a, mir-146b and/or mir-21 RNA. In some embodiments, the quantified miRNA expression levels in the malignant dataset, the benign dataset and the test result data of a test thyroid tissue sample can be expression levels of the following microRNAs: mir-328, mir-222, mir-197, and/or mir-21 RNA.

The test thyroid tissue sample can be a sample of a thyroid tissue or a thyroid nodule that is present in a subject. The test thyroid tissue sample can be of indeterminate diagnosis. For example, the test thyroid sample can be a thyroid tissue sample that has been evaluated, for example, by cytopathological or histological procedures and has been identified as being of indeterminate diagnosis (i.e., not definitively benign nor definitively malignant). In some embodiments, the test thyroid tissue sample is a fine needle aspiration sample.

The invention also provides a system comprising a processor, and a memory coupled to the processor and encoding one or more programs, wherein the one or more programs cause the processor to carry out any of the methods of the invention.

The invention further provides a computer program product for use in conjunction with a computer having a processor and a memory connected to the processor, the computer program product including a computer readable storage medium having a computer program mechanism encoded thereon, wherein the computer program mechanism may be loaded into the memory of the computer and cause the computer to carry out any of the methods of the invention.

DETAILED DESCRIPTION OF THE INVENTION

Figure 1A:
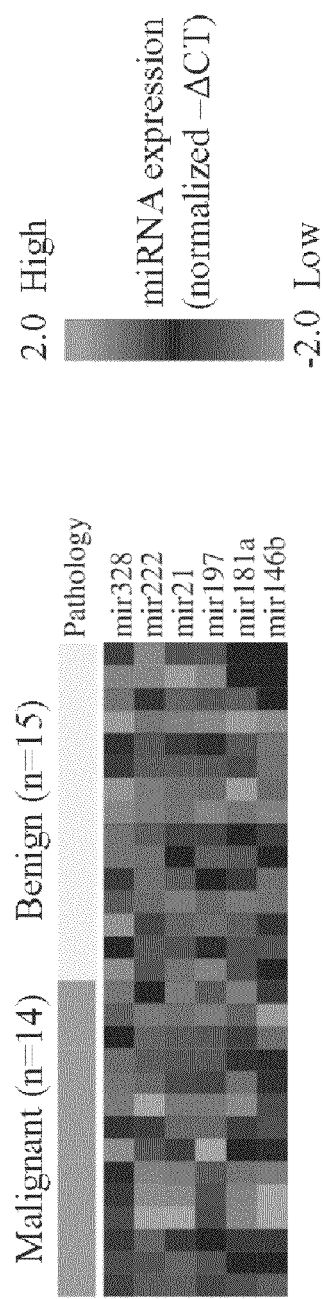
FIG. 1A-B shows normalized $-\Delta CTs$ for the Derivation Group (FIG. 1A) and Validation Group (FIG. 1B) for each miRNA using a heatmap representation of expression levels. In general, the lighter areas to the left (red in the original) represent higher levels of miRNA expression, while the lighter areas to right (green in the original) generally represent lower levels of miRNA expression. Darker areas indicate more moderate levels of miRNA expression. The bars above heatmaps indicate whether a sample is malignant (darker shade) or benign (lighter shade) as determined by pathology or by use of the predictive methods described herein.

The invention relates to methods for evaluating whether a test thyroid tissue sample is malignant or benign. In some embodiments, the expression levels of selected microRNAs are quantified and the quantified expression level data is evaluated versus a malignant dataset of quantified microRNA expression levels obtained from test thyroid tissue samples of patients having malignant thyroid cancer and/or a benign dataset of quantified microRNA expression levels obtained from thyroid tissue samples of patients not having malignant thyroid cancer. In some embodiments, the expression levels of the following microRNAs are evaluated: mir-328, mir-222, mir-197, mir-181a, mir-146b and/or mir-21 RNA against a malignant and/or benign dataset of expression levels of the same microRNAs. In other embodiments, the expression levels of the following microRNAs are evaluated: mir-328, mir-222, mir-197, and/or mir-21 RNA against a malignant and/or benign dataset of expression levels of the same microRNAs. An algorithm, processor and/or a computer can be employed to facilitate such evaluation.

Thyroid Tissue Samples

In some embodiments, tissue samples are obtained from a patient for testing. Such tissue samples are generally referred to as "test samples." As used herein, "obtaining a test sample" involves removing a sample of tissue from a patient, receiving a sample of tissue from a patient, receiving a patient's tissue sample from a physician, receiving a patient's tissue sample via mail delivery and/or removing a patient's tissue sample from a storage apparatus (e.g., a refrigerator or freezer) or a facility. Thus, obtaining a test sample can involve removal or receipt of the test sample directly from the patient, but obtaining a test sample can also include receipt of a test sample indirectly from a medical worker, from a storage apparatus/facility, from a mail delivery service after transportation from a medical facility, and any combination thereof. The test sample can therefore originate in one location, and be transported to another location where it is received and tested. Any of these activities or combinations of activities involves "obtaining a test sample."

The test, benign and malignant thyroid tissue samples can be collected from patients using any available procedure. For example, the thyroid tissue samples can be collected by fine needle aspiration or coarse needle biopsy. In general, the microRNA expression levels of test thyroid tissue samples are collected in a manner similar to benign and malignant thyroid tissue samples used as a basis for the benign and malignant datasets of the microRNA expression levels.

In some embodiments, the thyroid tissue samples are collected by fine needle aspiration. As used herein, "fine needle aspiration" involves the removal of a few clusters of individual thyroid cells by means of a small needle, for example, a 25-gauge needle. Several thyroid nodules can be sampled and/or collected. In some embodiments, when more than one thyroid nodule is sampled, the tissues from the different nodules are separately evaluated. Thyroid nodules that have recently grown in size may be of particular interest. The fine needle aspiration procedure can include examination and assessment of the sample cells by a cytopathologist (e.g., using a microscope and/or histological procedures).

Fine needle aspiration (which can include microscopic examination and assessment of the sample cells by a cytopathologist) typically results in a definitive classification of the test thyroid tissue sample in approximately 70-80% of cases, while the remaining 20-30% of samples are characterized as indeterminate (Cooper et al., Management guidelines for patients with thyroid nodules and differentiated thyroid cancer, Thyroid 16:109-42 (2006); Wang & Crapo, The epidemiology of thyroid disease and implications for screening. Endocrinol Metab Clin North Am 26:189-218 (1997)).

Thus, fine needle aspiration biopsy can lead to incorrect diagnosis. About three percent of the time, the biopsy result will be benign, but the nodule will actually be a cancer. This mistake is called a false-negative result and usually results from the fact that the needle was not inserted directly into the cancer. Either the needle missed the nodule or the needle sampled areas of the nodule that were benign, not cancerous. If a nodule is very small, it is possible to miss it completely with the needle. On the other hand, the larger a nodule is, the higher the probability of this sampling error, since only part of the nodule may be cancerous. The more experienced the physician is at performing these biopsies, the smaller the risk of missing the nodule or not sampling all areas. However, these risks can never be eliminated entirely.

Coarse needle biopsy involves the removal of a core of thyroid tissue from the nodule using a larger needle. In addition to providing information about individual cells, this method provides an architectural pattern of connection between cells. Unlike the fine needle aspiration procedure, which can be performed on all types of nodules, the nodule must be at least ¾ of an inch in size in order to successfully perform a coarse needle biopsy. Some studies have shown that those who have had a coarse needle biopsy are less likely to be recommended for surgery than those who have not had this type of biopsy.

In general, a coarse needle biopsy is more difficult to perform and there are few physicians with experience in this procedure. If a nodule is very low in the neck or if a patient is obese, it may be difficult to perform this biopsy from a technical standpoint. In addition, because the needle is large, there is a risk (usually less than 1%) of bleeding or injury to the windpipe or nerves controlling the vocal cords.

Experiments described herein demonstrate that test thyroid tissue samples are accurately identified as benign or malignant when the simpler, less intrusive fine needle aspiration procedure is used for collection of the samples.

MicroRNAs

MicroRNAs (miRNA) are single stranded non-coding small RNA segments, 19-23 nucleotides in length. Mature miRNAs operate via sequence-specific interaction with the 3' untranslated region of mRNA targets and thereby cause suppression of translation and mRNA decay (Bartel, Cell 136: 215-33 (2009)).

MicroRNAs have been shown to function as both tumor suppressors and oncogenes and may be useful for cancer classification and prognostication (Wiemer, Eur J Cancer 43:1529-44 (2007)). MicroRNAs have been reported to be dysregulated many human cancer types (Gao et al. Endocr J 57:81-86 2010; Menon & Khan J Clin Pathol 62:978-85 (2009); and Nikiforova et al. Endocr Pathol 20:85-91 (2009)). See also, He et al, Proc Natl Acad Sci USA 102:19075-80 (2005); Pallante et al. Endocr Relat Cancer 17:F91-104 (2010); and Sheu et al. Br J Cancer 102:376-82 (2010).

Experiments described herein elucidate the expression patterns of six miRNAs in indeterminate thyroid lesions sampled by fine needle aspiration and provide a means for differentiating benign from malignant thyroid tissue samples. In fact the methods described herein are particularly and surprisingly effective at differentiating benign from malignant indeterminate thyroid lesions.

In some embodiments, the expression levels of the following microRNAs are evaluated: mir-328, mir-222, mir-197, mir-21, mir-181a, and/or mir-146b RNA against a malignant and/or benign dataset of expression levels of the same microRNAs. In other embodiments, the accuracy of differentiating benign from malignant indeterminate thyroid lesions is improved by evaluating the expression levels of the following microRNAs: mir-328, mir-222, mir-197, and mir-21 RNA against a malignant and/or benign dataset of expression levels of the same microRNAs.

The expression levels of microRNAs can be evaluated by procedures available in the art, including procedures described herein, using probes and/or primers that bind to the selected microRNAs. Such probes and primers can be complementary and/or homologous to the selected microRNA sequences.

Sequences for various microRNAs are available from the National Center for Biotechnology Information (NCBI) database (see, e.g., the website at ncbi.nlm.nih.gov). For example, a nucleic acid sequence for the mir-328 microRNA (*Homo sapiens*) is available as accession number NR_029887.1 (GI: 262206326), and is reproduced below as SEQ ID NO:1.

```
  1 TGGAGTGGGG GGGCAGGAGG GGCTCAGGGA GAAAGTGCAT
 41 ACAGCCCCTG GCCCTCTCTG CCCTTCCGTC CCCTG
```

In its RNA form, mir-328 has the following sequence (SEQ ID NO:2).

```
  1 UGGAGUGGGG GGGCAGGAGG GGCUCAGGGA GAAAGUGCAU
 41 ACAGCCCUG GCCCUCUCUG CCCUUCCGUC CCCUG
```

Mir-328 is processed by removal of nucleotides from the 5' and 3' end, leaving a shorter mature mir-328 microRNA sequence spanning nucleotides 47-69, which has the following sequence (SEQ ID NO:3).

```
 47 CCUG GCCCUCUCUG CCCUUCCGU
```

A nucleic acid sequence for the mir-222 microRNA (*Homo sapiens*) is available as accession number NR_029636.1 (GI: 262206346), and is reproduced below as SEQ ID NO:4.

```
  1 GCTGCTGGAA GGTGTAGGTA CCCTCAATGG CTCAGTAGCC
 41 AGTGTAGATC CTGTCTTTCG TAATCAGCAG CTACATCTGG
 81 CTACTGGGTC TCTGATGGCA TCTTCTAGCT
```

In its RNA form, mir-222 has the following sequence (SEQ ID NO:5).

```
  1 GCUGCUGGAA GGUGUAGGUA CCCUCAAUGG CUCAGUAGCC
 41 AGUGUAGAUC CUGUCUUUCG UAAUCAGCAG CUACAUCUGG
 81 CUACUGGGUC UCUGAUGGCA UCUUCUAGCU
```

Mir-222 is processed by removal of nucleotides from the 5' and 3' end, leaving a shorter mature mir-222 microRNA sequence spanning nucleotides 69-89, which has the following sequence (SEQ ID NO:6).

```
 69 AG CUACAUCUGG CUACUGGGU
```

A nucleic acid sequence for the mir-197 microRNA (*Homo sapiens*) is available as accession number NR_029583.1 (GI: 262206094), and is reproduced below as SEQ ID NO:7.

```
  1 GGCTGTGCCG GGTAGAGAGG GCAGTGGGAG GTAAGAGCTC
 41 TTCACCCTTC ACCACCTTCT CCACCCAGCA TGGCC
```

In its RNA form, mir-197 has the following sequence (SEQ ID NO:8).

```
  1 GGCUGUGCCG GGUAGAGAGG GCAGUGGGAG GUAAGAGCUC
 41 UUCACCCUUC ACCACCUUCU CCACCCAGCA UGGCC
```

Mir-197 is processed by removal of nucleotides from the 5' and 3' end, leaving a shorter mature mir-197 microRNA sequence spanning nucleotides 48-69, which has the following sequence (SEQ ID NO:9).

```
 48 UUC ACCACCUUCU CCACCCAGC
```

A nucleic acid sequence for the mir-21 microRNA (*Homo sapiens*) is available as accession number NR_029493.1 (GI: 262205659), and is reproduced below as SEQ ID NO:10.

```
  1 TGTCGGGTAG CTTATCAGAC TGATGTTGAC TGTTGAATCT
 41 CATGGCAACA CCAGTCGATG GGCTGTCTGA CA
```

In its RNA form, mir-21 has the following sequence (SEQ ID NO:11).

```
  1 UGUCGGGUAG CUUAUCAGAC UGAUGUUGAC UGUUGAAUCU
 41 CAUGGCAACA CCAGUCGAUG GGCUGUCUGA CA
```

Mir-21 is processed by removal of nucleotides from the 5' and 3' end, leaving a shorter mature mir-21 microRNA sequence spanning nucleotides 8-29, which has the following sequence (SEQ ID NO:12).

```
  8 UAG CUUAUCAGAC UGAUGUUGA
```

A nucleic acid sequence for the mir-181a microRNA (*Homo sapiens*) is available as accession number NR_029626.1 (GI:262206301), and is reproduced below as SEQ ID NO:13.

```
  1 TGAGTTTTGA GGTTGCTTCA GTGAACATTC AACGCTGTCG
 41 GTGAGTTTGG AATTAAAATC AAAACCATCG ACCGTTGATT
 81 GTACCCTATG GCTAACCATC ATCTACTCCA
```

In its RNA form, mir-181a has the following sequence (SEQ ID NO:14).

```
  1 UGAGUUUUGA GGUUGCUUCA GUGAACAUUC AACGCUGUCG
 41 GUGAGUUUGG AAUUAAAAUC AAAACCAUCG ACCGUUGAUU
 81 GUACCCUAUG GCUAACCAUC AUCUACUCCA
```

Mir-181a is processed by removal of nucleotides from the 5' and 3' end, leaving a shorter mature mir-21 microRNA sequence spanning nucleotides 24-46, which has the following sequence (SEQ ID NO:15).

```
24 AACAUUC AACGCUGUCG GUGAGU
```

A nucleic acid sequence for the mir-146b microRNA (*Homo sapiens*) is available as accession number NR_030169.1 (GI:262205193), and is reproduced below as SEQ ID NO:16.

```
 1 CCTGGCACTG AGAACTGAAT TCCATAGGCT GTGAGCTCTA
41 GCAATGCCCT GTGGACTCAG TTCTGGTGCC CGG
```

In its RNA form, mir-146b has the following sequence (SEQ ID NO:17).

```
 1 CCUGGCACUG AGAACUGAAU UCCAUAGGCU GUGAGCUCUA
41 GCAAUGCCCU GUGGACUCAG UUCUGGUGCC CGG
```

Mir-146b is processed by removal of nucleotides from the 5' and 3' end, leaving a shorter mature mir-21 microRNA sequence spanning nucleotides 9-30, which has the following sequence (SEQ ID NO:18).

```
9 UG AGAACUGAAU UCCAUAGGCU
```

In some embodiments, expression of the following microRNA sequences was detected and/or quantified.

```
hsa-mir-197-3p
                                    (SEQ ID NO: 19)
UUCACCACCUUCUCCACCCAGC hsa-mir-21-5p
                                    (SEQ ID NO: 20)
UAGCUUAUCAGACUGAUGUUGA hsa-mir-222
                                    (SEQ ID NO: 21)
AGCUACAUCUGGCUACUGGGUCUC hsa-mir-328
                                    (SEQ ID NO: 22)
CUGGCCCUCUCUGCCCUUCCGU hsa-146b-5p
                                    (SEQ ID NO: 23)
UGAGAACUGAAUUCCAUAGGCU hsa-181a-5p
                                    (SEQ ID NO: 24)
AACAUUCAACGCUGUCGGUGAGU.
```

However, the methods described herein include quantification of the expression levels of any of the foregoing microRNAs.

Assays for Detecting and Quantifying RNA

Any technique known to one of skill in the art for detecting and measuring RNA expression levels can be used in accordance with the methods described herein. Non-limiting examples of such techniques include microarray analysis, Northern blotting, nuclease protection assays, RNA fingerprinting, polymerase chain reaction, ligase chain reaction, Qbeta replicase, isothermal amplification method, strand displacement amplification, transcription based amplification systems, quantitative nucleic acid amplification assays (e.g., polymerase chain reaction assays), combined reverse transcription/nucleic acid amplification, nuclease protection (SI nuclease or RNAse protection assays), Serial Analysis Gene Expression (SAGE), next generation sequencing, gene expression microarray, as well as other methods.

Polynucleotide microarrays can be used to simultaneously measure whether or not any of several microRNAs are expressed. Generally, microarrays include probes for a plurality of microRNAs informative for benign/malignancy determination, for a particular disease or condition, and, in particular, for individuals having specific combinations of genotypic or phenotypic characteristics of the disease or condition (i.e., that are prognosis-informative for a particular patient subset).

A standard Northern blot assay can be used to ascertain an RNA transcript size, and the relative amounts of mRNA in a sample, in accordance with conventional Northern hybridization techniques known to those persons of ordinary skill in the art. In Northern blots, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., a microRNA from a different species or genomic DNA fragments that might contain an exon) may be used as probes. The labeled probe can be a labeled cDNA; a full-length, single stranded labeled RNA or DNA, or a labeled fragment of that RNA or DNA sequence.

Such a RNA or DNA (or fragments therefore) may serve as a probe, for example, when it is at least 9, at least 10, at least 11, at least 12, at least 13, at least 14, at least 15, or at least 16 consecutive nucleotides in length. In some embodiments, the probe is about 9, about 10, about 11, about 12, about 13, about 14, about 15, about 16, about 17, about 18, about 19, about 20, about 21 or about 22 consecutive nucleotides in length. In further embodiments, the probe may be at least 20, at least 30, at least 50, or at least 70 consecutive nucleotides in length. The primers and/or probes can be less than about 80, less than about 70, less than about 60, less than about 50, less than about 45, less than about 40, less than about 39, less than about 38, less than about 37, less than about 36, less than about 35, less than about 34, less than about 33, less than about 32, less than about 31, or less than about 30 consecutive nucleotides in length.

The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. The radioactive label can be detected by any of the currently available counting procedures. Non-limiting examples of isotopes include $^3$H, $^{14}$C, $^{32}$P, $^{35}$S, $^{36}$Ci, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

Nuclease protection assays such as ribonuclease protection assays and S1 nuclease assays can be used to detect and quantify specific microRNAs. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 µg of sample RNA, compared with the 20-30 µg maximum of blot hybridizations.

A ribonuclease protection assay employs RNA probes. Oligonucleotides and other single-stranded DNA probes can only be used in assays containing S1 nuclease. The single-stranded, antisense probe must typically be completely homologous to target RNA to prevent cleavage of the probe: target hybrid by nuclease.

Serial Analysis Gene Expression (SAGE), which is described in e.g., Velculescu et al., 1995, *Science* 270:484-7; Carulli, et al., 1998, *Journal of Cellular Biochemistry Supplements* 30/31:286-96, can also be used to determine RNA abundances in a cell sample.

Quantitative reverse transcriptase PCR (qRT-PCR) can also be used to determine the expression profiles of microRNA genes (see, e.g., U.S. Patent Application Publication No. 2005/0048542A1). The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, commonly employed polymerases include the Taq DNA polymerase, which has a 5'-3' nuclease activity but lacks a 3'-5' proofreading endonuclease activity. TaqMan® PCR typically utilizes the 5'-nuclease activity of Taq or Tth polymerase to hydrolyze a hybridization probe bound to its target amplicon, but any enzyme with similar or equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™. Sequence Detection System™ (Perkin-Elmer-Applied Biosystems, Foster City, Calif., USA), or Lightcycler (Roche Molecular Biochemicals, Mannheim, Germany). In one embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system includes software for running the instrument and for analyzing the data.

In some embodiments, the quantitative RT-PCR assay data are presented as Ct values, also referred to as $\Delta$Ct thresholds. The $\Delta$Ct (cycle threshold) is defined as the number of cycles required for the fluorescent signal to cross a detectable threshold. The $\Delta$Ct is a measure of when the amount of RNA expressed exceeds background levels. Ct threshold levels are inversely proportional to the amount of target nucleic acid in the sample (i.e., the lower the Ct threshold the greater the amount of target nucleic acid in the sample). Fluorescence values are recorded during every cycle and represent the amount of product amplified to that point in the amplification reaction. The point when the fluorescent signal is first recorded as statistically significant is the threshold cycle ($\Delta$Ct).

To minimize errors and the effect of sample-to-sample variation, RT-PCR is often performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and $\beta$-actin.

A more recent variation of the RT-PCR technique is the real time quantitative PCR, which measures PCR product accumulation through a dual-labeled fluorogenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., Genome Research 6:986-994 (1996).

Methods of Assessing Whether a Test Thyroid Tissue Sample is Benign or Malignant As described herein the invention involves a method of assessing whether a test thyroid tissue sample is benign or malignant. Such methods can include:
  a. obtaining or determining a quantified expression level of at least one of the following microRNAs: mir-328, mir-222, mir-197, mir-181a, mir-146b and/or mir-21 RNA in the test thyroid tissue sample to obtain at least one test sample expression level;
  b. comparing the at least one test sample expression level to a malignant thyroid dataset and to a benign thyroid dataset;
  c. determining whether the at least one test sample expression level is statistically significantly within the malignant thyroid dataset or within the benign thyroid dataset to thereby assess whether the test thyroid tissue sample is benign or malignant;
    wherein the malignant thyroid dataset is a collection of quantified expression levels of mir-328, mir-222, mir- 197, mir-181a, mir-146b and/or mir-21 RNA from malignant thyroid tissue samples; and wherein the benign thyroid dataset is a collection of quantified expression levels of mir-328, mir-222, mir-197, mir-181a, mir-146b and/or mir-21 RNA from benign, healthy, and/or non-cancerous thyroid tissue samples.

In some embodiments, the expression levels are quantified for the following four microRNAs: mir-328, mir-222, mir-197, and mir-21 RNAs. These four miRNAs all appear to be involved to some extent in cell cycle control or cell proliferation. MicroRNA-222 has been shown to regulate p27kip1 (cyclin-dependant kinase inhibitor), which inhibits G1-S phase cell-cycle progression and serves as a checkpoint for cell proliferation (Visone et al., Endocr Relat Cancer 14:791-798 (2007)) (18). MicroRNA 197 and 328 appear to target a variety of genes that are involved in cell proliferation and apoptosis (Weber et al., J Clin Endocrinol Metab 91:3584-91 (2006)). MicroRNA 21 appears to target mRNAs encoding important cell cycle checkpoints regulators and also to be upregulated in thyroid and lung tumors harboring the RAS mutation (Frezzetti et al., Oncogene (2010); Jazdzewski et al., J Clin Endocrinol Metab (2010)).

As used herein the phrase "determining whether a test dataset of expression levels is significantly within a malignant thyroid dataset or within a benign thyroid dataset" in some embodiments involves actual measurement of test dataset expression levels, i.e., quantifying the expression levels of mir-328, mir-222, mir-197, mir-181a, mir-146b and/or mir-21 RNA in a test thyroid tissue sample from the patient and then assessing whether the those test dataset expression levels are significantly (e.g., statistically significantly) within a malignant thyroid dataset or within a benign thyroid dataset. In other embodiments, the phrase "determining whether a test dataset of expression levels is significantly within a malignant thyroid dataset or within a benign thyroid dataset" involves obtaining measurements of test dataset expression levels by directing another person or entity to make those measurements, and then assessing whether the those test dataset expression levels are significantly (e.g., statistically significantly) within a malignant thyroid dataset or within a benign thyroid dataset. In further embodiments, the phrase "determining whether a test dataset of expression levels is significantly within a malignant thyroid dataset or within a benign thyroid dataset" involves obtaining measurements of test dataset expression levels by directing another person or entity to make those measurements, and having that other person or entity assess whether the those test dataset expression levels are significantly (e.g., statistically significantly) within a malignant thyroid dataset or within a benign thyroid dataset. The other (second) person or entity can then report to the person or entity that requested the determination and/or assessment. Thus, the determining step can be performed directly by one person or entity; or alternatively, the determining step can be performed indirectly by a second person or entity who is acting at the request of a first person or entity. The first person or entity can assess whether the test dataset expression levels are significantly (e.g., statistically significantly) within a malignant thyroid dataset or within a benign thyroid dataset. Alternatively, the first person or entity can direct the second person or entity to assess whether the test dataset expression levels are significantly (e.g., statistically significantly) within a malignant thyroid dataset or within a benign thyroid dataset.

Experiments described herein demonstrate that the inventors' methods accurately differentiate benign from malignant indeterminate lesions obtained by fine needle aspiration with a specificity of 86%. When Hürthle cell neoplasms were excluded from the dataset(s) the specificity improved to 95%.

Those of cell in the art can readily recognize Hürthle cell neoplasms by available cytological, cytopathological and/or histological procedures. For example, the cytological features for Hürthle cell neoplasms include hypercellularity with a predominance of Hürthle cells (usually >75%), few or no lymphocytes, and scanty or absent colloid. Hürthle cells are typically large and polygonal in shape, with indistinct cell borders. They have a large pleomorphic hyperchromatic nucleus, a prominent nucleolus, and intensely pink, fine, granular cytoplasm with hematoxylin-eosin staining.

Methods described herein using the mir-328, mir-222, mir-197, and mir-21 miRNA panel are essentially 100% sensitive for malignant pathology of indeterminate fine needle aspiration thyroid lesions. Thus, it would be reasonable to recommend a total thyroidectomy if malignancy is predicted by the procedures described herein. Furthermore, the methods described herein are also 95% predictive for benign pathology of indeterminate lesions (when Hurthle Cell lesions are excluded). In view of the low risk of a false negative result (only about 5% for indeterminate lesions), a diagnostic hemithyroidectomy with its inherent risks and costs can be avoided in patients in the majority of cases. Instead, the physician may recommend monitoring the lesion or further testing at a later date.

Previously, 20-30% of fine needle aspiration samples were characterized as indeterminate, and many of those 'indeterminate' patients were subjected to surgeries that may not have been necessary.

In summary, the inventors have developed a predictive methods using four miRNAs (miR-222, 328, 197 and 21) that is 100% sensitive and 86% specific for differentiating malignant from benign indeterminate FNA thyroid lesions. When Hurthle cell neoplasms were excluded from the analysis, the model had an improved specificity of 95% and an overall accuracy of 97% while retaining a sensitivity of 100% for malignant lesions.

Use of the methods desribed herein with the panel of four to six miRNAs in daily clinical practice is realistic and feasible and can be performed in an easy and rapid way by quantifying miRNA expression levels and using statistical analysis as described herein for classification. For example, a benign/malignancy predictor based on any of such methods can be constructed using the microRNA expression levels of malignant and benign patients as a training dataset. Such a benign/malignancy predictor can then be used to determine whether a patient may have malignant or benign thyroid cancer based on the expression levels of various microRNAs in thyroid test tissue samples obtained from the patient.

For example, the following Table A shows ΔCt threshold values for expression of various microRNA in tissue samples from patients with established malignant (M) and benign (B) thyroid tissues; these values can serve as malignant and benign datasets, respectively, for statistical analysis and statistical training purposes.

TABLE A

Exemplary Malignant and Benign Datasets

| GROUP | mir328 | mir222 | mir21 | mir197 |
|---|---|---|---|---|
| M | −1.52 | −3.01 | −8.91 | −2.13 |
| M | −2.67 | −3.35 | −9.07 | −0.52 |
| M | −2.39 | −8.08 | −7.86 | −1.55 |
| M | −2.7 | −12.26 | −12.91 | −2.21 |
| M | −2.35 | −10.65 | −10.75 | −2.35 |

TABLE A-continued

Exemplary Malignant and Benign Datasets

| GROUP | mir328 | mir222 | mir21 | mir197 |
|---|---|---|---|---|
| M | −1.84 | −9.85 | −10.1 | −0.3 |
| M | −4.58 | −7.45 | −8.07 | −7.61 |
| M | −1.68 | −6.42 | −5.08 | −2.9 |
| M | −3.87 | −12.76 | −9.9 | −3.35 |
| M | −3.78 | −8.38 | −8.35 | −2.11 |
| M | −0.27 | −3.04 | −8.73 | −0.36 |
| M | −2.06 | −8.17 | −8.77 | −0.4 |
| M | −3.2 | −9.18 | −9.6 | −3.51 |
| M | 0.04 | −5.63 | −4.03 | −0.23 |
| B | −4.52 | −3.51 | −9.86 | −3.69 |
| B | −2.11 | −3.11 | −5.83 | −1.35 |
| B | −4.8 | −6.61 | −9.14 | −2.97 |
| B | −0.78 | −1.92 | −4.15 | 0.04 |
| B | −1.55 | −1.89 | −5.5 | −1.37 |
| B | −3.75 | −8.78 | −7.12 | −2.7 |
| B | −3.74 | −7.9 | −8.12 | −2.12 |
| B | 0.68 | −0.76 | −4.6 | 1.09 |
| B | 1.23 | −0.89 | −4.79 | 0.23 |
| B | −1.55 | −2.97 | −5.52 | −0.39 |
| B | −2.29 | −7.49 | −6.72 | −1.26 |
| B | 2.55 | −1.29 | −3.79 | 1.29 |
| B | −3.75 | −4.75 | −9.12 | −2.46 |
| B | 0.61 | 0.06 | −0.985 | 1.245 |
| B | −2.49 | 0.045 | −5.845 | −0.39 |

Artificial Neural Network

In some embodiments, a neural network is used in the benign/malignancy predictor. A neural network can be constructed from one or more dataset of microRNA expression levels. A neural network can be a two-stage regression or classification model. The neural network can be an algorithm that facilitates multidimensional analysis of three or more variables. A neural network can have a layered structure that includes a layer of input units (and the bias) connected by a layer of weights to a layer of output units. For regression, the layer of output units typically includes just one output unit. However, neural networks can handle multiple quantitative responses in a seamless fashion.

In multilayer neural networks, there are input units (input layer), hidden units (hidden layer), and output units (output layer). There is, furthermore, a single bias unit that is connected to each unit other than the input units. Neural networks are described in Duda et al., 2001, *Pattern Classification*, Second Edition, John Wiley & Sons, Inc., New York; and Hastie et al., 2001, *The Elements of Statistical Learning*, Springer-Verlag, New York.

The basic approach to the use of neural networks is to start with an untrained dataset, present a training pattern amongst, for example, microRNA expression levels from training patients, to the input layer, and to pass signals through the net and determine the output, for example, criteria for determining the malignancy/benign status of the (training) patients, at the output layer. These outputs are then compared to the target values; any difference corresponds to an error. This error or criterion function is some scalar function of the weights and is minimized when the network outputs match the desired outputs. Thus, the weights are adjusted to reduce this measure of error. For regression, this error can be sum-of-squared errors. For classification, this error can be either squared error or cross-entropy (deviation). See, e.g., Hastie et al., 2001, *The Elements of Statistical Learning*, Springer-Verlag, New York.

Three commonly used training protocols are stochastic, batch, and on-line. In stochastic training, patterns are chosen randomly from the training set and the network weights are updated for each pattern presentation. Multilayer nonlinear networks trained by gradient descent methods such as stochastic back-propagation perform a maximum-likelihood estimation of the weight values in the model defined by the network topology. In batch training, all patterns are presented to the network before learning takes place. Typically, in batch training, several passes are made through the training data. In online training, each pattern is presented once and only once to the net.

In some embodiments, consideration is given to starting values for weights. If the weights are near zero, then the operative part of the sigmoid commonly used in the hidden layer of a neural network (see, e.g., Hastie et al., 2001, *The Elements of Statistical Learning*, Springer-Verlag, New York) is roughly linear, and hence the neural network collapses into an approximately linear model. In some embodiments, starting values for weights are chosen to be random values near zero. Hence the model starts out nearly linear, and becomes nonlinear as the weights increase. Individual units localize to directions and introduce nonlinearities where needed. Use of exact zero weights leads to zero derivatives and perfect symmetry, and the algorithm never moves. Alternatively, starting with large weights often leads to poor solutions.

Since the scaling of inputs determines the effective scaling of weights in the bottom layer, it can have a large effect on the quality of the final solution. Thus, in some embodiments, at the outset all expression values are standardized to have mean zero and a standard deviation of one. This ensures all inputs are treated equally in the regularization process, and allows one to choose a meaningful range for the random starting weights. With standardization inputs, it is typical to take random uniform weights over the range [−0.7, +0.7].

A recurrent problem in the use of networks having a hidden layer is the optimal number of hidden units to use in the network. The number of inputs and outputs of a network are determined by the problem to be solved. In the present invention, the number of inputs for a given neural network can be the number of microRNA markers in the dataset. The number of output states for the neural network will typically be just one. However, in some embodiment more than one output is used so that more than just two states can be defined by the network. If too many hidden units are used in a neural network, the network will have too many degrees of freedom and if trained too long, there is a danger that the network will overfit the data. If there are too few hidden units, the training set cannot be learned. Generally speaking, however, it is better to have too many hidden units than too few. With too few hidden units, the model might not have enough flexibility to capture the nonlinearities in the data; with too many hidden units, the extra weight can be shrunk towards zero if appropriate regularization or pruning, as described below, is used. In typical embodiments, the number of hidden units is somewhere in the range of 4 to 100, with the number increasing with the number of inputs and number of training cases.

One general approach to determining the number of hidden units to use is to apply a regularization approach. In the regularization approach, a new criterion function is constructed that depends not only on the classical training error, but also on classifier complexity. Specifically, the new criterion function penalizes highly complex models; searching for the minimum in this criterion is to balance error on the training set with error on the training set plus a regularization term, which expresses constraints or desirable properties of solutions:

$$J = J_{pat} + \lambda J_{reg}.$$

The parameter $\lambda$ is adjusted to impose the regularization more or less strongly. In other words, larger values for $\lambda$ will tend to shrink weights towards zero: typically cross-validation with a validation set is used to estimate λ. This validation set can be obtained by setting aside a random subset of the training population. Other forms of penalty can also be used, for example the weight elimination penalty (see, e.g., Hastie et al., 2001, *The Elements of Statistical Learning*, Springer-Verlag, New York).

Another approach to determine the number of hidden units to use is to eliminate—prune—weights that are least needed. In one approach, the weights with the smallest magnitude are eliminated (set to zero). Such magnitude-based pruning can work, but is nonoptimal; sometimes weights with small magnitudes are important for learning and training data. In some embodiments, rather than using a magnitude-based pruning approach, Wald statistics are computed. The fundamental idea in Wald Statistics is that they can be used to estimate the importance of a hidden unit (weight) in a model. Then, hidden units having the least importance are eliminated (by setting their input and output weights to zero). Two algorithms in this regard are the Optimal Brain Damage (OBD) and the Optimal Brain Surgeon (OBS) algorithms that use second-order approximation to predict how the training error depends upon a weight, and eliminate the weight that leads to the smallest increase in training error.

Optimal Brain Damage and Optimal Brain Surgeon share the same basic approach of training a network to local minimum error at weight w, and then pruning a weight that leads to the smallest increase in the training error. The predicted functional increase in the error for a change in full weight vector δw is:

$$\delta J = \left\{\frac{\delta J}{\partial w}\right\}^t \cdot \delta w + \frac{1}{2}\delta w^t \cdot \frac{\partial^2 J}{\partial w^2} \cdot \delta w + O(\|\delta w\|^3)$$

where $$\frac{\partial^2 J}{\partial w^2}$$

is the Hessian matrix. The first term vanishes because we are at a local minimum in error; third and higher order terms are ignored. The general solution for minimizing this function given the constraint of deleting one weight is:

$$\partial w = -\frac{w_q}{[\mathbb{H}^{-1}]_{qq}}\mathbb{H}^{-1} \cdot u_q$$

and $$Lq = \frac{1}{2} - \frac{w_q}{[\mathbb{H}^{-1}]_{qq}}$$

Here, $u_q$ is the unit vector along the qth direction in weight space and $L_q$ is approximation to the saliency of the weight q—the increase in training error if weight q is pruned and the other weights updated δw. These equations require the inverse of $\mathbb{H}$. One method to calculate this inverse matrix is to start with a small value, $\mathbb{H}_0^{-1} = \alpha^{-1} I$, where α is a small parameter—effectively a weight constant. Next the matrix is updated with each pattern according to $$\mathbb{H}_{m+}^{-1} = \mathbb{H}_m^{-1} - \frac{\mathbb{H}_m^{-1} \mathbb{X}_{m+1} \mathbb{X}_{m+1}^T \mathbb{H}_m^{-1}}{\frac{n}{a_m} \mathbb{X}_{m+1}^T \mathbb{H}_m^{-1} \mathbb{X}_{m+1}}$$

where the subscripts correspond to the pattern being presented and $a_m$ decreases with m. After the full training set has been presented, the inverse Hessian matrix is given by $H^{-1} = H_n^{-1}$. In algorithmic form, the Optimal Brain Surgeon method is:

$$q^* \leftarrow \underset{q}{\mathrm{argmin}}\ w_q^2 \Big/ (2\lfloor H^{-1}\rfloor_{qq})\ (\text{saliency } Lq)$$

$$w \leftarrow w - \frac{w_q^*}{[H^{-1}]_{q^*q^*}} H^{-1} e_q^*\ (\text{saliency } Lq)$$

The Optimal Brain Damage method is computationally simpler because the calculation of the inverse Hessian matrix in line 3 is particularly simple for a diagonal matrix. The above algorithm terminates when the error is greater than a criterion initialized to be θ. Another approach is to change line 6 to terminate when the change in J(w) due to elimination of a weight is greater than some criterion value.

In some embodiments, a back-propagation neural network (see, for example Abdi, 1994, "A neural network primer," J. Biol System. 2, 247-283) containing a single hidden layer of ten neurons (ten hidden units) found in EasyNN-Plus version 4.0 g software package (Neural Planner Software Inc.) is used. In a specific example, parameter values within the EasyNN-Plus program are set as follows: a learning rate of 0.05, and a momentum of 0.2. In some embodiments in which the EasyNN-Plus version 4.0 g software package is used, "outlier" samples are identified by performing twenty independently-seeded trials involving 20,000 learning cycles each.

Support Vector Machine

In some embodiments of the present invention, support vector machines (SVMs) are used to classify subjects using expression profiles of marker genes described in the present invention. General description of SVM can be found in, for example, Cristianini and Shawe-Taylor, 2000, *An Introduction to Support Vector Machines*, Cambridge University Press, Cambridge, Boser et al., 1992, "A training algorithm for optimal margin classifiers, in *Proceedings of the 5th Annual ACM Workshop on Computational Learning Theory*, ACM Press, Pittsburgh, Pa., pp. 142-152; Vapnik, 1998, *Statistical Learning Theory*, Wiley, New York; Duda, *Pattern Classification*, Second Edition, 2001, John Wiley & Sons, Inc.; Hastie, 2001, *The Elements of Statistical Learning*, Springer, New York; and Furey et al., 2000, Bioinformatics 16, 906-914, each of which is specifically incorporated by reference herein in its entirety. Applications of SVM in biological applications are described in Jaakkola et al., *Proceedings of the 7th International Conference on Intelligent Systems for Molecular Biology*, AAAI Press, Menlo Park, Calif. (1999); Brown et al., *Proc. Natl. Acad. Sci.* 97(1):262-67 (2000); Zien et al., *Bioinformatics*, 16(9):799-807 (2000); Furey et al., *Bioinformatics*, 16(10):906-914 (2000)

In one approach, when a SVM is used, the gene expression data is standardized to have mean zero and unit variance and the members of a training population are randomly divided into a training set and a test set. For example, in one embodiment, two thirds of the members of the training population are placed in the training set and one third of the members of the training population are placed in the test set. The expression values for a selected set of microRNAs is used to train the SVM. Then the ability for the trained SVM to correctly classify members in the test set is determined. In some embodiments, this computation is performed several times for a given selected set of microRNAs. In each iteration of the computation, the members of the training population are randomly assigned to the training set and the test set. Then, the quality of the combination of molecular markers is taken as the average of each such iteration of the SVM computation.

Support vector machines map a given set of binary labeled training data to a high-dimensional feature space and separate the two classes of data with a maximum margin hyperplane. In general, this hyperplane corresponds to a nonlinear decision boundary in the input space. Let $X \in R_0 \subseteq \Re^l$ be the input vectors, $y \in \{-1,+1\}$ be the labels, and
$\phi: R_0 \to F$ be the mapping from input space to feature space. Then the SVM learning algorithm finds a hyperplane (w,b) such that the quantity $$\gamma = \min y_i \{\langle w, \phi(\mathbb{X}_i) \rangle - b\}$$

is maximized, where the vector w has the same dimensionality as F, b is a real number, and $\gamma$ is called the margin. The corresponding decision function is then $$f(X) = \text{sign}(\langle w, \phi(\mathbb{X}_i) \rangle - b)$$

This minimum occurs when $$w = \sum_i \alpha_i y_i \phi(X_i)$$

where $\{\alpha_i\}$ are positive real numbers that maximize $$\sum_i \alpha_i - \sum_{ij} \alpha_i \alpha_j y_i y_j \langle \phi(X_i), \phi(X_j) \rangle$$

subject to $$\sum_i \alpha_i y_i = 0, \alpha_i > 0$$

The decision function can equivalently be expressed as $$f(\mathbb{X}) = \text{sign}(\Sigma \alpha_i y_i \langle \phi(X_i), \phi(\mathbb{X}) \rangle - b)$$

From this equation it can be seen that the $\alpha_i$ associated with the training point $\mathbb{X}_i$ expresses the strength with which that point is embedded in the final decision function. A remarkable property of this alternative representation is that only a subset of the points will be associated with a non-zero $\alpha_i$. These points are called support vectors and are the points that lie closest to the separating hyperplane. The sparseness of the $\alpha$ vector has several computational and learning theoretic consequences. It is important to note that neither the learning algorithm nor the decision function needs to represent explicitly the image of points in the feature space, $\phi(\mathbb{X})$, since both use only the dot products between such images, $\phi(X_i), \phi(X_j)$. Hence, if one were given a function $K(\mathbb{X}, \mathbb{Y}) = (\phi(\mathbb{X}), \phi(\mathbb{Y}))$, one could learn and use the maximum margin hyperplane in the feature space without ever explicitly performing the mapping. For each continuous positive definite function $K(\mathbb{X}, \mathbb{Y})$ there exists a mapping $\phi$ such that $K(\mathbb{X}, \mathbb{Y}) = \langle \phi(\mathbb{X}), \phi(\mathbb{X}) \rangle$ for all $\mathbb{X}, \mathbb{Y} \in R_0$ (Mercer's Theorem).

The function $K(\mathbb{X}, \mathbb{Y})$ is called the kernel function. The use of a kernel function allows the support vector machine to operate efficiently in a nonlinear high-dimensional feature spaces without being adversely affected by the dimensionality of that space. Indeed, it is possible to work with feature spaces of infinite dimension. Moreover, Mercer's theorem makes it possible to learn in the feature space without even knowing $\phi$ and F. The matrix $K_{ij} = \langle \phi(\mathbb{X}_i), \phi(\mathbb{X}_j) \rangle$ is called the kernel matrix. Finally, note that the learning algorithm is a quadratic optimization problem that has only a global optimum. The absence of local minima is a significant difference from standard pattern recognition techniques such as neural networks. For moderate sample sizes, the optimization problem can be solved with simple gradient descent techniques. In the presence of noise, the standard maximum margin algorithm described above can be subject to overfitting, and more sophisticated techniques should be used. This problem arises because the maximum margin algorithm always finds a perfectly consistent hypothesis and does not tolerate training error. Sometimes, however, it is necessary to trade some training accuracy for better predictive power. The need for tolerating training error has led to the development the soft-margin and the margin-distribution classifiers. One of these techniques replaces the kernel matrix in the training phase as follows:

$$K \leftrightarrow K + \lambda I$$

while still using the standard kernel function in the decision phase. By tuning one can control the training error, and it is possible to prove that the risk of misclassifying unseen points can be decreased with a suitable choice of $\lambda$.

If instead of controlling the overall training error one wants to control the trade-off between false positives and false negatives, it is possible to modify K as follows:

$$K \leftrightarrow K + \lambda D$$

where D is a diagonal matrix whose entries are either $d^+$ or $d^-$, in locations corresponding to positive and negative examples. It is possible to prove that this technique is equivalent to controlling the size of the $\alpha_i$ in a way that depends on the size of the class, introducing a bias for larger $\alpha_i$ in the class with smaller d. This in turn corresponds to an asymmetric margin; i.e., the class with smaller d will be kept further away from the decision boundary. In some cases, the extreme imbalance of the two classes, along with the presence of noise, creates a situation in which points from the minority class can be easily mistaken for mislabeled points. Enforcing a strong bias against training errors in the minority class provides protection against such errors and forces the SVM to make the positive examples support vectors. Thus, choosing $$d^+ = \frac{1}{n^+}$$

and $$d^+ = \frac{1}{n^-}$$

provides a heuristic way to automatically adjust the relative importance of the two classes, based on their respective cardinalities. This technique effectively controls the trade-off between sensitivity and specificity.

In the methods described herein, a linear kernel can be used. The similarity between two marker profiles $\mathbb{X}$ and $\mathbb{Y}$ can be the dot product $\mathbb{X} \cdot \mathbb{Y}$. In one embodiment, the kernel is $$K(\mathbb{X}, \mathbb{Y}) = \mathbb{X} \cdot \mathbb{Y} + 1$$

In another embodiment, a kernel of degree d is used $$K(\mathbb{X}, \mathbb{Y}) = (\mathbb{X} \cdot \mathbb{Y} + 1)^d$$

where d can be an integer of 2 or more (e.g., 2, 3, 4, 5, . . . ).

In still another embodiment, a Gaussian kernel can be used $$K(\mathbb{X}, \mathbb{Y}) = \exp\left(\frac{-|X-Y|^2}{2\sigma^2}\right)$$

where σ is the width of the Gaussian.

In further embodiments, the kernel function can be a radial basis kernel function shown below:

$$K(x_i, x_j) = \exp(-\gamma \|x_i - x_j\|^2)$$

where: γ>0 and where $x_i$ and $x_j$ are vectors containing expression values describing lesions. The γ parameter specifies the shape of the RBF function. A cost parameter can be employed that controls the tradeoff between allowing training errors and forcing rigid classification margins. The cost parameter effectively creates a soft margin that permits some misclassifications, thus allowing for a more generalizable classifier.

A radial basis kernel (γ) ranging, for example, from about 0.1 to 4.0 can employed. In some embodiments, a cost parameter of about 20 to about 150 can be employed. In other embodiments, the radial basis kernel γ variable ranges from about 0.2 to about 3.0, or from about 0.3 to about 2.0, or from about 0.35 to about 1.0, or from about 0.4 to about 0.8, or from about 0.45 to about 0.6. In further embodiments, the cost parameter variable ranges from about 25 to about 140, or from about 30 to about 120, or from about 40 to about 100, or from about 45 to about 90, or from about 50 to about 80, or from about 55 to about 75, or from about 60 to about 70, or from about 61 to about 68, or from about 62 to about 67, or from about 63 to about 66, or from about 63 to about 65. As illustrated herein, a support vector machine algorithm with a radial basis kernel γ variable of about 0.5 and a cost variable of about 64 provided a combination of ΔCT thresholds for four microRNAs that discriminated between malignant and benign lesions.

Computer Systems

The invention also provides a system comprising a processor, and a memory coupled to the processor and encoding one or more programs, wherein the one or more programs cause the processor to carry out a method described above. See, e.g., FIG. 2.

The invention also provides a computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out a method described above.

Figure 2:
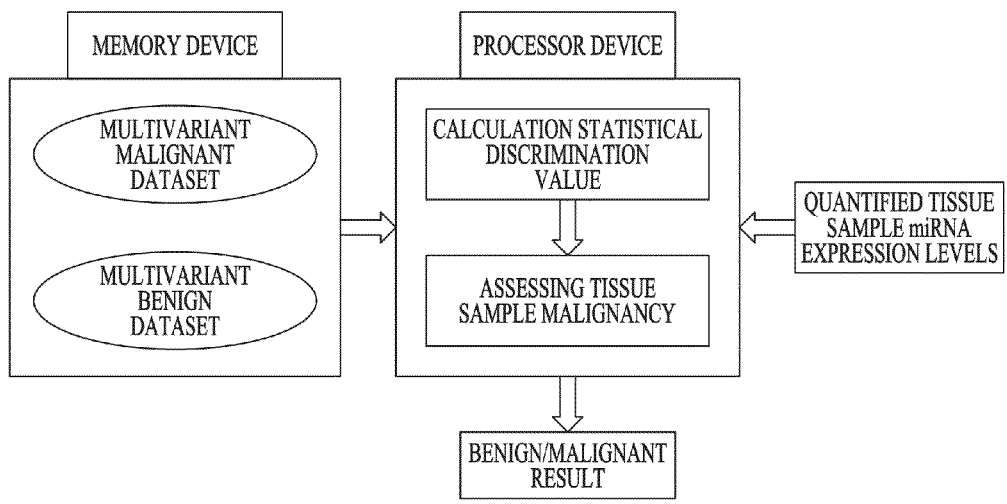
FIG. 2 is a schematic diagram of an example of a system for assessing test thyroid tissue samples using the methods and malignant/benign discrimination criteria described herein.

For example, FIG. 2 illustrates a system for performing the methods described herein such a system can include (i) a memory device that stores a multivariant malignant dataset and a multivariant benign dataset, as well as (ii) a processor device capable of calculating one or more discrimination values that discriminate between malignant and benign thyroid lesions, and assessing quantified test tissue sample miRNA expression levels to determine whether the test tissue sample is benign or malignant.

The system can include both the memory device and the processor.

In other embodiments, the memory device can be separate from the processor. For example, the memory device can be a computer program product for use in conjunction with a computer having a processor and a memory connected to the processor. The computer program product can include a computer readable storage medium having a computer program mechanism encoded thereon, wherein the computer program mechanism may be loaded into the memory of the computer and cause the computer to carry out any of the methods of the invention. The computer program product can include a multivariant malignant dataset and a multivariant benign dataset.

Therapy

The methods described herein can be used for determining whether a thyroid cancer patient may benefit from treatment such as surgery or chemotherapy. For example, one aspect of the invention is a method for determining whether a thyroid cancer patient should be treated with surgery or chemotherapy, by determining whether the test tissue sample from a patient has malignant or benign cells. If the patient's test tissue sample has malignant cancer cells, the patient may undergo surgery for removal of thyroid tissues and/or undergo chemotherapy.

If a patient is determined to be one likely to benefit from chemotherapy, a suitable chemotherapeutic regimen may be prescribed for the patient. Chemotherapy can be performed using any one or a combination of the anti-cancer drugs known in the art, including but not limited to any radioactive drug, topoisomerase inhibitor, DNA binding agent, anti-metabolite, ionizing radiation, or a combination of two or more of such known DNA damaging agents. In some embodiments, the anti-cancer agent is radioactive iodine.

A topoisomerase inhibitor that can be used in conjunction with the invention can be, for example, a topoisomerase I (Topo I) inhibitor, a topoisomerase II (Topo II) inhibitor, or a dual topoisomerase I and II inhibitor. A topo I inhibitor can be from any of the following classes of compounds: camptothecin analogue (e.g., karenitecin, aminocamptothecin, lurtotecan, topotecan, irinotecan, BAY 56-3722, rubitecan, GI14721, exatecan mesylate), rebeccamycin analogue, PNU 166148, rebeccamycin, TAS-103, camptothecin (e.g., camptothecin polyglutamate, camptothecin sodium), intoplicine, ecteinascidin 743, J-107088, pibenzimol. Examples of preferred topo I inhibitors include but are not limited to camptothecin, topotecan (hycaptamine), irinotecan (irinotecan hydrochloride), belotecan, or an analogue or derivative thereof.

A topo II inhibitor that can be used in conjunction with the invention can be, for example, from any of the following classes of compounds: anthracycline antibiotics (e.g., carubicin, pirarubicin, daunorubicin citrate liposomal, daunomycin, 4-iodo-4-doxydoxorubicin, doxorubicin, n,n-dibenzyl daunomycin, morpholinodoxorubicin, aclacinomycin antibiotics, duborimycin, menogaril, nogalamycin, zorubicin, epirubicin, marcellomycin, detorubicin, annamycin, 7-cyanoquinocarcinol, deoxydoxorubicin, idarubicin, GPX-100, MEN-10755, valrubicin, KRN5500), epipodophyllotoxin compound (e.g., podophyllin, teniposide, etoposide, GL331, 2-ethylhydrazide), anthraquinone compound (e.g., ametantrone, bisantrene, mitoxantrone, anthraquinone), ciprofloxacin, acridine carboxamide, amonafide, anthrapyrazole antibiotics (e.g., teloxantrone, sedoxantrone trihydrochloride, piroxantrone, anthrapyrazole, losoxantrone), TAS-103, fostriecin, razoxane, XK469R, XK469, chloroquinoxaline sulfonamide, merbarone, intoplicine, elsamitrucin, CI-921, pyrazoloacridine, elliptinium, amsacrine. Examples of preferred topo II inhibitors include but are not limited to doxorubicin (Adriamycin), etoposide phosphate (etopofos), teniposide, sobuzoxane, or an analogue or derivative thereof.

DNA binding agents that can be used in conjunction with the invention include but are not limited to DNA groove binding agent, e.g., DNA minor groove binding agent; DNA crosslinking agent; intercalating agent; and DNA adduct forming agent. A DNA minor groove binding agent can be an anthracycline antibiotic, mitomycin antibiotic (e.g., porfiromycin, KW-2149, mitomycin B, mitomycin A, mitomycin C), chromomycin A3, carzelesin, actinomycin antibiotic (e.g., cactinomycin, dactinomycin, actinomycin F1), brostallicin, echinomycin, bizelesin, duocarmycin antibiotic (e.g., KW 2189), adozelesin, olivomycin antibiotic, plicamycin, zinostatin, distamycin, MS-247, ecteinascidin 743, amsacrine, anthramycin, and pibenzimol, or an analogue or derivative thereof. DNA crosslinking agents include but are not limited to antineoplastic alkylating agent, methoxsalen, mitomycin antibiotic, psoralen. An antineoplastic alkylating agent can be a nitrosourea compound (e.g., cystemustine, tauromustine, semustine, PCNU, streptozocin, SarCNU, CGP-6809, carmustine, fotemustine, methylnitrosourea, nimustine, ranimustine, ethylnitrosourea, lomustine, chlorozotocin), mustard agent (e.g., nitrogen mustard compound, such as spiromustine, trofosfamide, chlorambucil, estramustine, 2,2,2-trichlorotriethylamine, prednimustine, novembichin, phenamet, glufosfamide, peptichemio, ifosfamide, defosfamide, nitrogen mustard, phenesterin, mannomustine, cyclophosphamide, melphalan, perfosfamide, mechlorethamine oxide hydrochloride, uracil mustard, bestrabucil, DHEA mustard, tallimustine, mafosfamide, aniline mustard, chlomaphazine; sulfur mustard compound, such as bischloroethylsulfide; mustard prodrug, such as TLK286 and ZD2767), ethylenimine compound (e.g., mitomycin antibiotic, ethylenimine, uredepa, thiotepa, diaziquone, hexamethylene bisacetamide, pentamethylmelamine, altretamine, carzinophilin, triaziquone, meturedepa, benzodepa, carboquone), alkylsulfonate compound (e.g., dimethylbusulfan, Yoshi-864, improsulfan, piposulfan, treosulfan, busulfan, hepsulfam), epoxide compound (e.g., anaxirone, mitolactol, dianhydrogalactitol, teroxirone), miscellaneous alkylating agent (e.g., ipomeanol, carzelesin, methylene dimethane sulfonate, mitobronitol, bizelesin, adozelesin, piperazinedione, VNP40101M, asaley, 6-hydroxymethylacylfulvene, EO9, etoglucid, ecteinascidin 743, pipobroman), platinum compound (e.g., ZD0473, liposomal-cisplatin analogue, satraplatin, BBR 3464, spiroplatin, ormaplatin, cisplatin, oxaliplatin, carboplatin, lobaplatin, zeniplatin, iproplatin), triazene compound (e.g., imidazole mustard, CB 10-277, mitozolomide, temozolomide, procarbazine, dacarbazine), picoline compound (e.g., penclomedine), or an analogue or derivative thereof. Examples of preferred alkylating agents include but are not limited to cisplatin, dibromodulcitol, fotemustine, ifosfamide (ifosfamid), ranimustine (ranomustine), nedaplatin (latoplatin), bendamustine (bendamustine hydrochloride), eptaplatin, temozolomide (methazolastone), carboplatin, altretamine (hexamethylmelamine), prednimustine, oxaliplatin (oxalaplatinum), carmustine, thiotepa, leusulfon (busulfan), lobaplatin, cyclophosphamide, bisulfan, melphalan, and chlorambucil, or analogues or derivatives thereof.

Intercalating agents can be an anthraquinone compound, bleomycin antibiotic, rebeccamycin analogue, acridine, acridine carboxamide, amonafide, rebeccamycin, anthrapyrazole antibiotic, echinomycin, psoralen, LU 79553, BW A773U, crisnatol mesylate, benzo(a)pyrene-7,8-diol-9,10-epoxide, acodazole, elliptinium, pixantrone, or an analogue or derivative thereof, etc.

DNA adduct forming agents include but are not limited to enediyne antitumor antibiotic (e.g., dynemicin A, esperamicin A1, zinostatin, dynemicin, calicheamicin gamma 1I), platinum compound, carmustine, tamoxifen (e.g., 4-hydroxy-tamoxifen), psoralen, pyrazine diazohydroxide, benzo(a)pyrene-7,8-diol-9,10-epoxide, or an analogue or derivative thereof.

Anti-metabolites include but are not limited to cytosine, arabinoside, floxuridine, fluorouracil, mercaptopurine, Gemcitabine, and methotrexate (MTX).

Kits

Another aspect of the invention is one or more kits for determining malignant/benign status of a test tissue sample. The kits of the present invention comprise one or more probes and/or primers each capable of specifically binding to a sequence of at least 15, 20, 25, 30, 40, 50 nucleotides, or any number of nucleotides between 13-50, in a selected microRNA. The probes may be part of an array. Alternatively, the probes or primers may be packaged separately and/or individually. In some embodiments, the probes or primers may be detectably labeled.

The microRNA to be detected with the kits can be mir-328, mir-222, mir-197, mir-181a, mir-146b and/or mir-21 RNA. In some embodiments, the microRNA to be detected with the kits can be mir-328, mir-222, mir-197, and/or mir-21 RNA.

Additional reagents can be included in the kits. For example, the kits may also contain reagents for determining the expression levels of microRNAs in a test tissue sample. Such reagents can include reagents for isolating, storing and detecting microRNAs. For example, the kits can include reagents and enzymes for nucleic acid amplification and/or for reverse transcription of microRNAs. The kits may also include reagents such as solutions stabilizing RNA, solutions for purifying RNA, buffers, or other reagents that can be used in obtaining the expression levels of microRNAs in a test tissue sample. Prevention of the action of microorganisms can be ensured by the inclusion of various antibacterial and antifungal agents, for example, paraben, chlorobutanol, phenol sorbic acid, and the like. It may also be desirable to include agents such as solvents for RNA, reducing agents (e.g., beta-mercaptoethanol), RNA stabilizing reagents (e.g., reagents for inhibiting ribonucleases, disrupting tissues, precipitating RNA, and the like).

In further embodiments, the kits can include a computer program product for use in conjunction with a computer system and the methods described herein. A computer program mechanism can be embedded in the computer program product. The computer program product can, for example, be a device with a computer program mechanism encoded thereon, where the computer program mechanism may be loaded into the memory of a computer and cause the computer to carry out at least one step of a method for assessing the malignant/benign status of a test thyroid tissue sample. For example, the device can be a computer readable storage medium, a flash memory, a compact disc (CD), a digital versatile disc, digital video disc, or an article of manufacture that tangibly comprise a computer program and memory storage. In some embodiments, the computer program product can be a computer readable storage medium. In such kits, the computer program mechanism can include instructions for determining malignant/benign status of a test tissue sample, where microRNA expression levels in the test tissue sample are obtained with the reagents of the kits.

In other embodiments, the kits can include a system, such as a computer, having a central processing unit and a memory coupled to the central processing unit (see, e.g., FIG. 2). The memory may store instructions for determining the malignant/benign status of a test tissue sample and the processor may evaluate microRNA expression levels. The memory can also store a malignant dataset and a benign dataset for comparison to microRNA expression levels detected in the test tissue sample.

The kits can also include a chemotherapeutic or anti-cancer agent, for example, any of the chemotherapeutic or anti-cancer agents described herein.

Example

This Example shows that quantified miRNA expression levels can be used to accurately assign benign versus malignant status to thyroid test tissue samples, including thyroid samples previously determined to be of indeterminate status by other procedures.

Materials and Methods

Differential expression of 6 miRNAs (mir-222, mir-181, mir-146b, mir-328, mir-197 and mir-21) were initially measured in 29 ex-vivo indeterminate fine needle aspiration samples and used to develop a predictive model (Derivation Group). This model was then validated on an independent set of 72 prospectively collected indeterminate fine needle aspiration samples (Validation Group).

Derivation Group

After approval from the Institutional Review Board (IRB) of Weill Cornell Medical College was obtained, written informed consent was collected from patients for the use of clinical specimens for research. One hundred eighty one (181) patients with indeterminate lesions that underwent surgery were identified. Of those, 14 indeterminate fine needle aspiration lesions with malignant final histopathology were identified and placed in a tumor bank. An additional 15 indeterminate lesions with benign final histopathology were randomly selected to match the malignant group. The numbers of benign (52%) and malignant (48%) lesions in the derivation set were kept equal in order to train the statistical model in recognizing benign and malignant lesions equally. All fine needle aspiration specimens used for the derivation set were taken from ex-vivo thyroid tissue samples after thyroidectomy was performed (Tables 1 and 2).

TABLE 1

Demographics and Pathological Characteristics of Derivation and Validation Groups

|  | Derivative Group | Validation Group |
|---|---|---|
| Age (Mean ± SD) | 50 ± 15 | 55 ± 16 |
| Sex |  |  |
| Male | 3 | 13 |
| Female | 26 | 59 |
| Tumor Size in cm (Mean ± SD) | 2.7 ± 1.7 | 2.8 ± 1.7 |
| Range | 0.8-6 | 0.7-7.4 |
| Surgery |  |  |
| Total Thyroidectomy | 12 | 35 |
| Hemi Thyroidectomy | 17 | 37 |
| Completion Thyroidectomy | 4 | 9 |
| FNA Pathology* |  |  |
| Follicular lesion of undetermined significance | 17 | 32 |
| Follicular Neoplasm | 9 | 23 |
| Hurthle Cell Neoplasm | 3 | 13 |
| Suspicious for Malignancy | 0 | 4 |
| Final Pathology# |  |  |
| CPTC | 4 | 8 |
| Poorly Differentiated PTC | 0 | 1 |
| FVPTC | 8 | 8 |

TABLE 1-continued

Demographics and Pathological Characteristics of Derivation and Validation Groups

|  | Derivative Group | Validation Group |
|---|---|---|
| FTC | 2 | 4 |
| Hurthle Cell Cancer | 0 | 1 |
| FA | 13 | 9 |
| HPN | 2 | 41 |
| Thyroiditis | 3 | 19 |

*Classification according to The NCI Thyroid Fine-Needle-Aspiration State of the Science Conference Scheme.
Final Pathology
CPTC: Classic Variant of Papillary Thyroid Cancer,
FVPTC: Follicular Variant of Papillary Thyroid Cancer,
FTC: Follicular Thyroid Cancer,
FA: Follicular Adenoma

TABLE 2

FNA and final diagnoses of 29 ex-vivo specimens (Derivation Group)

| Sample | FNA Diagnosis* | Nodule Size | Surgery† | Final Diagnosis# | Thyroiditis^ |
|---|---|---|---|---|---|
| 1 | Follicular Neoplasm | 2 | TT | FVPTC | No |
| 2 | Follicular lesion of undetermined significance | 2 | TT | FVPTC | No |
| 3 | Follicular lesion of undetermined significance | 2 | TT | CPTC | No |
| 4 | Follicular Neoplasm | 3.6 | TT | FTC | Yes |
| 5 | Follicular lesion of undetermined significance | 0.8 | HT | FVPTC | No |
| 6 | Hurthle Cell Neoplasm | 2.3 | TT | FVPTC, oncocytic variant | Yes |
| 7 | Follicular lesion of undetermined significance | 4.8 | HT + CT | FTC | No |
| 8 | Follicular lesion of undetermined significance | 4 | HT + CT | CPTC, cribiform variant | No |
| 9 | Follicular lesion of undetermined significance | 1.4 | HT | FVPTC | Yes |
| 10 | Follicular lesion of undetermined significance | 1.3 | TT | FVPTC | No |
| 11 | Follicular lesion of undetermined significance | 1 | HT | CPTC | No |
| 12 | Follicular lesion of undetermined significance | 1.4 | HT + CT | FVPTC | No |
| 13 | Hurthle Cell Neoplasm | 1.3 | HT + CT | FVPTC, oncocytic variant | No |
| 14 | Follicular lesion of undetermined significance | 2 | TT | CPTC | No |
| 15 | Hurthle Cell Neoplasm | 6 | HT | FA | No |
| 16 | Follicular Neoplasm | 2.3 | HT | FA | No |
| 17 | Follicular lesion of undetermined significance | 1.5 | HT | FA | No |
| 18 | Follicular Neoplasm | 2 | HT | FA | No |
| 19 | Follicular lesion of undetermined significance | 8 | HT | FA | No |

TABLE 2-continued

FNA and final diagnoses of 29 ex-vivo specimens
(Derivation Group)

| Sample | FNA Diagnosis* | Nodule Size | Surgery† | Final Diagnosis# | Thyroiditis^ |
|---|---|---|---|---|---|
| 20 | Follicular Neoplasm | 2.4 | HT | FA | No |
| 21 | Follicular lesion of undetermined significance | 4.2 | HT | FA | No |
| 22 | Follicular lesion of undetermined significance | 2.5 | TT | FA, oncocytic variant | No |
| 23 | Follicular Neoplasm | 1.1 | HT | FA | No |
| 24 | Follicular lesion of undetermined significance | 2.5 | TT | FA | No |
| 25 | Follicular Neoplasm | 1.5 | HT | FA | No |
| 26 | Follicular lesion of undetermined significance | 2.5 | TT | FA, myxoid features | No |
| 27 | Follicular Neoplasm | 2 | HT | FA | No |
| 28 | Follicular lesion of undetermined significance | 5 | TT | Hyperplastic Nodule | No |
| 29 | Follicular Neoplasm | 5 | TT | Hyperplastic Nodule | No |

*Classification according to The NCI Thyroid Fine-Needle-Aspiration State of the Science Conference Scheme.
†Surgery Performed: TT = Total Thyroidectomy, HT = Hemithyroidectomy, CT = Completion Thyroidectomy.
Final Diagnosis: PTC: Classic Variant of Papillary Thyroid Cancer, FVPTC: Follicular Variant of Papillary Thyroid Cancer, FTC: Follicular Thyroid Cancer, FA: Follicular Adenoma;
^Thyroiditis—Yes: Chronic Lymphocytic Thyroiditis, not meeting criteria for Hashimoto's or Grave's Thyroiditis, No: Absence of Thyroiditis Fine Needle Aspiration Sampling and Data Collection After thyroidectomy was performed, a 25-gauge needle was inserted in the thyroid nodule and 2 to 3 passages were used to collect the cytology specimen, which was then suspended in RLT-lysis Buffer, RNA later solution (Qiagen Inc., Valencia, Calif., USA) or Trizol (Invitrogen, Carlsbad, Calif.). RLT Lysis Buffer from Qiagen was used most frequently. The specimens were then snap frozen in liquid nitrogen and stored at −80° C. A cytopathologist reviewed all fine needle aspiration samples before surgery and an endocrine pathologist reviewed all surgery specimens. Only unequivocal cytological cases were included in this study. Final diagnosis, FNA diagnosis, age, sex, tumor size and location, FNA location, surgical procedure, extrathyroidal extension, angiolymphatic invasion and lymph node metastasis were recorded for each patient sample and entered into the tumor bank data sheet.

MicroRNA Selection, Extraction, Reverse Transcription and Real-Time-PCR

MicroRNAs were selected that, by initial testing, were differentially expressed between normal thyroid tissue or Follicular Adenoma (FA) and the following Classic Variant of Papillary Thyroid Cancer (CPTC), Follicular Variant of Papillary Thyroid Cancer (FVPTC) and Follicular Thyroid Cancer (FTC). Ultimately 6 miRNAs were selected for further analysis: mir-328, mir-222, mir-197, mir-181a, mir-146b and mir-21.

Primers were used to detect and quantify the following microRNA sequences:

hsa-mir-197-3p
(SEQ ID NO: 19)
UUCACCACCUUCUCCACCCAGC hsa-mir-21-5p
(SEQ ID NO: 20)
UAGCUUAUCAGACUGAUGUUGA hsa-mir-222
(SEQ ID NO: 21)
AGCUACAUCUGGCUACUGGGUCUC hsa-mir-328
(SEQ ID NO: 22)
CUGGCCCUCUCUGCCCUUCCGU hsa-146b-5p
(SEQ ID NO: 23)
UGAGAACUGAAUUCCAUAGGCU hsa-181a-5p
(SEQ ID NO: 24)
AACAUUCAACGCUGUCGGUGAGU.

Expression levels of mir-328, mir-222, mir-197, mir-181a, mir-146b and mir-21 were determined in fine needle aspiration specimens using Real-Time-PCR. MicroRNAs were extracted and reverse transcribed to cDNA according to standard protocols using the MirVana Kit (Ambion Inc.), the mirPremier Kit (Sigma Aldrich, St Louis Mo.) or the microRNA Purification Kit (Norgen Biotek Corp, Canada). The quantity and integrity of microRNA yield was assessed using the NanoDrop™ (NanoDrop Technologies, Willmington, Del.) and Bioanalyzer 2100 and RNA 6000 Nano/Pico LabChip® (Agilent Technologies, Palo Alto, Calif.). This method yielded RNA concentrations from 2 to 184 ng/μl. Reverse transcription was performed for each microRNA (TaqMan MicroRNA gene-expression array kit, Applied Biosystems, Inc) using 10 ng RNA for 15 μl of reverse transcription reaction; 1.33 μl of cDNA was then used for each 20 μl PCR reaction.

A quantitative reverse-transcriptase-polymerase-chain-reaction (RT-PCR) assay was used to measure miRNA levels using the TaqMan MicroRNA gene-expression assay kit (Applied Biosystems, Foster City, Calif., Part Number: 4427975; Assay IDs: 001093, 002276, 000543, 000543, 000543). RT-PCR was performed using an ABI PRISM 7000 Sequence Detection System. A total of 45 cycles of amplification were performed, each cycle consisting of 15 sec at 95° C. and 1 min at 60° C. according to the standard protocol. Control amplification was performed in all samples in triplicate. RNU6B was used as a housekeeping gene (control) and ΔCt values were recorded and used for data analysis.

Statistical Analysis and Derivation Group Model Development

Several methodologies were evaluated for building statistical models that can predict benign versus malignant status in indeterminate thyroid FNA lesions based on expression profiles of the 6 miRNAs. These methodologies were regression trees, logistic regression, linear discriminant analysis (LDA), quadratic discriminant analysis (QDA) and support vector machines (SVM) with different kernel functions (Duda R. Pattern Classification. 2nd Edition ed: Willey-Interscience (2000); Venables W. Modern Applied Statistics with S (Statistics and Computing): Springer (2010)). Support vector machines (SVM) are well suited for two-class or multi-class pattern recognition (Weston and Watkins, Proceedings of the Seventh European Symposium On Artificial Neural Networks (1999); Vapnik, The Nature of Statistical Learning Theory (Springer, New York, 1995); Vapnik, Statistical Learning Theory, Wiley, New York (1998); Burges, Data Mining and Knowledge Discovery, 2(2):955-974, (1998)).

By representing lesions as data points in a multidimensional space, and combining the expression levels of several miRNAs in a linear or non-linear manner, these approaches find decision surfaces that best separate malignant and benign lesions.

Support Vector Machines identify the hyperplane such that the distance (also called margin) between the hyperplane and the closest data points is maximized. The data points that are exactly the margin distance away from the hyperplane are called 'support vectors.' Because in many cases no separating hyperplane exists, some data points are allowed to be on the wrong side of their margin. The extent to which such flexibility is allowed is controlled by a cost parameter C>0. Moreover, a set of variables describing lesions can be expanded by mapping the original variables to a higher dimensional space using a non-linear function. Such mapping is obtained using kernel functions. A commonly used kernel function is the radial basis function kernel, shown below:

$$K(x_i,x_j)=\exp(-\gamma\|x_i-x_j\|^2)$$

where: $\gamma>0$ and where $x_i$ and $x_j$ are vectors containing expression values describing lesions.

The $\gamma$ parameter specifies the shape of the radial basis kernal function; the cost parameter controls the tradeoff between allowing training errors and forcing rigid classification margins. In essence, the cost parameter effectively creates a soft margin that permits some misclassifications, thus allowing for a more generalizable classifier. Both of the $\gamma$ and cost parameters were obtained using cross-validation.

More extensive descriptions of Support Vector Machines and other approaches used here have been described previously (Duda R. Pattern Classification. 2nd Edition ed: Willey-Interscience (2000); Venables W. Modern Applied Statistics with S (Statistics and Computing): Springer (2010)).

Using these methodologies and specific parameter choices (e.g. for SVMs), models were trained using all 29 samples and variable subsets of the 6 miRNAs were used. The predictive accuracy of each of these models was estimated using leave-one-out cross-validation (Duda R. Pattern Classification. 2nd Edition ed: Willey-Interscience (2000); Venables W. Modern Applied Statistics with S (Statistics and Computing): Springer (2010)). Feature selection was performed using both backward elimination and forward addition procedures using the 6 miRNAs. SVM kernel functions (linear, radial-basis) and parameter values were also explored and selected using cross-validation. All statistical procedures were implemented using the R statistical analysis language and software. The e1071, MASS and rpart R third-party libraries were used for SVM, LDA and regression trees, respectively.

Validation Group

After model selection, 72 consecutive specimens were collected prospectively in an in-vivo fashion using standard ultrasound-guided transcutaneous fine needle aspiration technique. Briefly, 1 to 2 passes were obtained with a 25-gauge needle and cytologic smears were made. Samples from both the clinic and the presurgical fine needle aspirations were then obtained from the residual material in the needle after the cytologic smears were made. All nodules were indeterminate lesions and no other selection criteria were applied except that the patient had to be going to surgery. All patients were euthyroid and none required preoperative treatment with thyroxine. The validation group consisted of 22 indeterminate lesions with malignant final pathology (30.5%) and 50 indeterminate lesions (69.5%) with benign final pathology (Tables 1 and 3). This benign to malignant sample ratio is consistent with the ratio reported in the literature for indeterminate FNA lesions, namely 20-30% for malignant and 70-80% for benign pathology (Gharib, Endocr Pract 2004; 10:31-9 (2004); Hegedus, N Engl J Med 2004; 351:1764-71 (2004); Layfield et al. Cytopathology 21:75-85 (2010); Nikiforov et al., J Clin Endocrinol Metab 94:2092-8 (2009); Xing et al., J Clin Oncol 27:2977-82 (2009)).

Sixteen indeterminate FNA samples were obtained from Johns Hopkins Hospital, of which 3 were malignant and 13 were benign on final pathology. Thirty-three samples were obtained in surgery clinic and thirty-nine FNA samples were obtained in the operating room prior to the surgical incision. All samples were obtained under identical conditions using ultrasound guidance. Cytologic smears were prepared for all pre-surgical samples at the time of biopsy to assure an adequate sample. All pre-surgical cytology samples were reviewed by a cytopathologist in a blinded fashion and all proved to be indeterminate lesions with identical features to the prior outside office FNA. An endocrine pathologist reviewed the histopathology of all specimens. None of the 72 FNA samples collected in vivo for validation were used for model selection or training.

TABLE 3

FNA and final diagnoses of 72 in-vivo specimens (Validation Group)

| Sample | FNA Diagnosis* | Nodule Size | Surgery[†] | Final Diagnosis[#] | Thyroiditis[^] |
|---|---|---|---|---|---|
| 1 | Follicular lesion of undetermined significance | 0.7 | HT | CPTC | No |
| 2 | Follicular lesion of undetermined significance | 1.5 | HT + CT | FVPTC | No |
| 3 | Follicular lesion of undetermined significance | 2.9 | TT | CPTC | Yes |
| 4 | Follicular lesion of undetermined significance | 1.9 | TT | CPTC | No |
| 5 | Follicular lesion of undetermined significance | 1.3 | TT | FVPTC | No |
| 6 | Follicular lesion of undetermined significance | 0.8 | TT | CPTC | Grave's |
| 7 | Hurthle Cell Neoplasm | 2.5 | TT | Hurthle Cell Cancer | No |

TABLE 3-continued

FNA and final diagnoses of 72 in-vivo specimens (Validation Group)

| Sample | FNA Diagnosis* | Nodule Size | Surgery† | Final Diagnosis# | Thyroiditis^ |
|---|---|---|---|---|---|
| 8 | Follicular lesion of undetermined significance | 7 | HT + CT | Poorly Differentiated PTC | No |
| 9 | Follicular Neoplasm | 1.7 | HT + CT | FVPTC | No |
| 10 | Follicular Neoplasm | 6 | HT + CT | FTC | Hashimoto's |
| 11 | Follicular lesion of undetermined significance | 3.4 | HT + CT | FVPTC | No |
| 12 | Suspicious for Malignancy | 1 | TT | CPTC | No |
| 13 | Suspicious for Malignancy | 1.1 | TT | CPTC | No |
| 14 | Follicular Neoplasm | 1.9 | HT + CT | FVPTC | No |
| 15 | Follicular Neoplasm | 7.4 | TT | FVPTC | No |
| 16 | Follicular Neoplasm | 6 | TT | FTC | Hashimoto's |
| 17 | Follicular lesion of undetermined significance | 2 | TT | FVPTC | No |
| 18 | Hurthle Cell Neoplasm | 1.1 | HT + CT | FTC | Yes |
| 19 | Follicular lesion of undetermined significance | 2.2 | HT + CT | FVPTC | No |
| 20 | Suspicious for Malignancy | 2 | TT | CPTC | No |
| 21 | Follicular Neoplasm | 2.9 | HT + CT | FTC | Yes |
| 22 | Follicular Neoplasm | 1 | TT | CPTC | Yes |
| 23 | Hurthle Cell Neoplasm | 6 | HT | FA | No |
| 24 | Follicular lesion of undetermined significance | 2.5 | TT | FA, myxoid features | No |
| 25 | Hurthle Cell Neoplasm | 3.2 | TT | Hyperplastic Nodule | No |
| 26 | Follicular lesion of undetermined significance | 1.3 | HT | Hyperplastic Nodule | Yes |
| 27 | Follicular lesion of undetermined significance | 3.1 | HT | Hyperplastic Nodule | No |
| 28 | Follicular lesion of undetermined significance | 4 | TT | Hyperplastic Nodule | Yes |
| 29 | Follicular Neoplasm | 5 | HT | Hyperplastic Nodule | No |
| 30 | Follicular Neoplasm | 2.6 | TT | Hyperplastic Nodule | No |
| 31 | Follicular Neoplasm | 3.4 | HT | Hyperplastic Nodule | No |
| 32 | Follicular Neoplasm | 1.3 | HT | Hyperplastic Nodule | No |
| 33 | Follicular lesion of undetermined significance | 5.3 | HT | Hyperplastic Nodule | No |
| 34 | Follicular lesion of undetermined significance | 3 | TT | Hyperplastic Nodule | Hashimoto's |
| 35 | Follicular lesion of undetermined significance | 1.5 | HT | Hyperplastic Nodule | No |
| 36 | Follicular lesion of undetermined significance | 2 | HT | Hyperplastic Nodule | Yes |
| 37 | Follicular lesion of undetermined significance | 1 | TT | Hyperplastic Nodule | Hashimoto's |
| 38 | Follicular lesion of undetermined significance | 4.5 | TT | Hyperplastic Nodule | No |
| 39 | Follicular lesion of undetermined significance | 2 | HT | Hyperplastic Nodule | No |
| 40 | Hurthle Cell Neoplasm | 4.5 | HT | Hyperplastic Nodule | No |

TABLE 3-continued

FNA and final diagnoses of 72 in-vivo specimens (Validation Group)

| Sample | FNA Diagnosis* | Nodule Size | Surgery† | Final Diagnosis# | Thyroiditis^ |
|---|---|---|---|---|---|
| 41 | Follicular lesion of undetermined significance | 3.5 | HT | Hyperplastic Nodule | No |
| 42 | Follicular lesion of undetermined significance | 1.1 | TT | Hyperplastic Nodule | No |
| 43 | Follicular lesion of undetermined significance | 6 | HT | FA, atypia | No |
| 44 | Follicular lesion of undetermined significance | 7 | HT | Hyperplastic Nodule | No |
| 45 | Suspicious for Malignancy | 1.6 | TT | FA | Hashimoto's |
| 46 | Follicular Neoplasm | 4.5 | HT | Hyperplastic Nodule | No |
| 47 | Hurthle Cell Neoplasm | 1.3 | TT | Hyperplastic Nodule, oncocytic features | Yes |
| 48 | Follicular lesion of undetermined significance | 3.8 | TT | Hyperplastic Nodule | Yes |
| 49 | Follicular lesion of undetermined significance | 2.1 | TT | Hyperplastic Nodule | No |
| 50 | Follicular lesion of undetermined significance | 5 | TT | Hyperplastic Nodule | No |
| 51 | Follicular Neoplasm | 3.2 | TT | FA | Yes |
| 52 | Follicular Neoplasm | 2.3 | TT | Hyperplastic Nodule | No |
| 53 | Follicular lesion of undetermined significance | 5 | HT | Hyperplastic Nodule | Yes |
| 54 | Hurthle Cell Neoplasm | 2.9 | HT | Hyperplastic Nodule, oncocytic features | No |
| 55 | Follicular Neoplasm | 2.4 | HT | Hyperplastic Nodule | Yes |
| 56 | Follicular Neoplasm | 2.8 | HT | Hyperplastic Nodule | Yes |
| 57 | Follicular lesion of undetermined significance | 2 | HT | Hyperplastic Nodule | No |
| 58 | Hurthle Cell Neoplasm | 1.7 | TT | Hyperplastic Nodule, oncocytic features | No |
| 59 | Follicular lesion of undetermined significance | 2 | HT | Hyperplastic Nodule | No |
| 60 | Follicular lesion of undetermined significance | 1.8 | HT | Hyperplastic Nodule | No |
| 61 | Hurthle Cell Neoplasm | 1.1 | TT | Hyperplastic Nodule, oncocytic features | No |
| 62 | Follicular lesion of undetermined significance | 1.3 | HT | Hyperplastic Nodule | No |
| 63 | Follicular Neoplasm | 1 | TT | Hyperplastic Nodule | No |
| 64 | Follicular lesion of undetermined significance | 1.6 | HT | Hyperplastic Nodule | No |
| 65 | Hurthle Cell Neoplasm | 2.8 | TT | FA oncocytic features | No |
| 66 | Hurthle Cell Neoplasm | 2.7 | TT | FA oncocytic features | No |
| 67 | Follicular Neoplasm | 1.8 | HT | FA | No |
| 68 | Hurthle Cell Neoplasm | 1 | TT | Hurthle Cell Adenoma | No |

TABLE 3-continued

FNA and final diagnoses of 72 in-vivo specimens (Validation Group)

| Sample | FNA Diagnosis* | Nodule Size | Surgery† | Final Diagnosis# | Thyroiditis^ |
|---|---|---|---|---|---|
| 69 | Follicular Neoplasm | 4.3 | HT | FA | Hashimoto's |
| 70 | Hurthle Cell Neoplasm | 1.2 | TT | Hyperplastic Nodule | No |
| 71 | Follicular Neoplasm | 1.4 | HT | Hyperplastic Nodule | No |
| 72 | Follicular Neoplasm | 4.5 | TT | Hyperplastic Nodule | No |

*Classification according to The NCI Thyroid Fine-Needle-Aspiration State of the Science Conference Scheme.
†Type of Surgery: TT = Total Thyroidectomy, HT = Hemithyroidectomy, CT = Completion Thyroidectomy.
Final Diagnosis: CPTC: Classic Variant of Papillary Thyroid Cancer, FVPTC: Follicular Variant of Papillary Thyroid Cancer, FTC: Follicular Thyroid Cancer, FA: Follicular Adenoma;
^Thyroiditis—Yes: Chronic Lymphocytic Thyroiditis, not meeting criteria for Hashimoto's or Grave's Thyroiditis, No: Absence of Thyroiditis Results A total of 101 indeterminate thyroid FNA samples were included in this study, 29 ex-vivo samples in the derivation group and 72 in-vivo samples in the validation group (Tables 1-3).

Figure 1B:
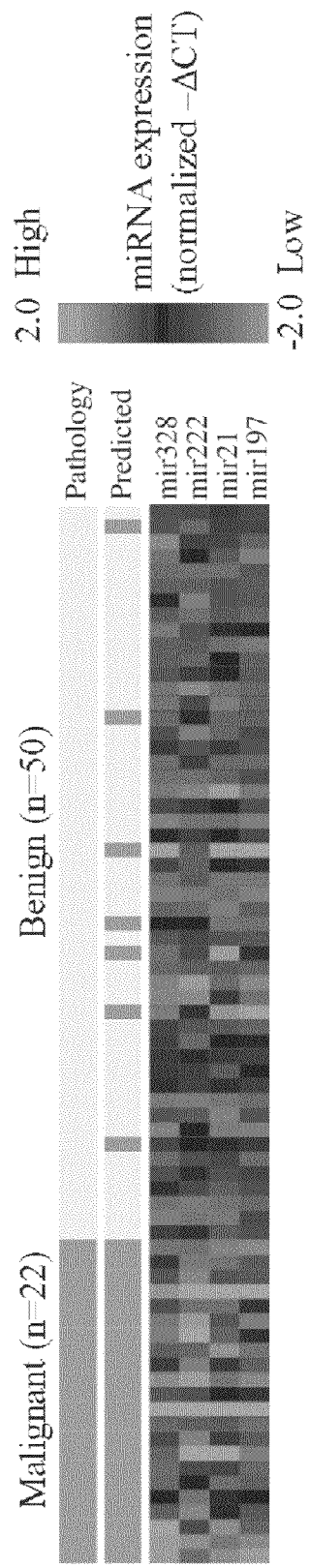

Statistical Models Accurately Predict Benign Versus Malignant Fine Needle Aspiration Sample Status within the Derivation Group Expression levels of 6 miRNAs with identified differential expression in thyroid cancer were measured on 29 samples from the derivation group using RT-PCR as described above. $\Delta CTs$ were used as expression measures, using RNU6B as housekeeping reference gene. Normalized $-\Delta CTs$ are shown in FIG. 1 (Normalized $-\Delta CTs$ for the Derivation Group (A) and Validation Group (B) for each miRNA using a heatmap representation). Additionally, mean $\Delta CT$ values for each miRNA for samples in the derivation group are shown in Table A.

Using non-parametric Wilcoxon rank-sum tests, the inventors found that four miRNAs were differentially expressed between malignant and benign lesions; these included miR-222 ($p<0.005$), miR-21 ($p<0.03$), miR-181a ($p<0.04$) and miR-146b ($p<0.03$). MicroRNA expression levels of mir-197 ($p=0.3$) and mir-328 ($p=0.6$) were not statistically significantly different.

To investigate how to use miRNA expression values to achieve maximum accuracy in predicting benign versus malignant status of indeterminate thyroid lesions on FNA, the inventors developed predictive models using several statistical methodologies, ranging from simple linear approaches (logistic regression) to more complicated non-linear ones (Support Vector Machines with non-linear kernel functions). Predictive performances were assessed using cross-validation. For each statistical methodology used, the inventors determined whether using subsets of miRNAs instead of all 6 miRNAs improved predictive performances.

The results of these analyses are shown in Table 4.

TABLE 4

Statistical models and their predictive performances in the ex-vivo FNA samples (Derivation Group)

| Methodology | miRNAs selected | % Accuracy training set | % Accuracy cross-validation | % Sensitivity cross-validation | % Specificity cross-validation |
|---|---|---|---|---|---|
| Regression tree | miR-21 | 78% | 78% | 69% | 86% |
| Logistic regression | miR-21 | 78% | 78% | 69% | 86% |
| LDA* | miR-21 | 78% | 78% | 69% | 86% |
| SVM^ with linear kernel, cost = 1 | miR-21, miR-328 | 78% | 78% | 71% | 85% |
| QDA† | miR-328, miR-222, miR-21, miR-197 | 93% | 85% | 86% | 85% |
| SVM^ with radial basis kernel, $\gamma = 0.5$, cost = 64 | miR-328, miR-222, miR-21, miR-197 | 100% | 86% | 86% | 87% |

*Linear Discriminant Analysis,
^Support Vector Machines,
†Quadratic Discriminant Analysis In Table 4, the $\gamma$ parameter specifies the shape of the RBF function, while the cost parameter controls the tradeoff between allowing training errors and forcing rigid classification margins. The cost parameter effectively creates a soft margin that permits some misclassifications, thus allowing for a more generalizable classifier. Both parameters are obtained using cross-validation.

The regression tree methodology provided easily interpretable results because it identifies the combination of $\Delta CT$ thresholds that best discriminate between malignant and benign lesions. To determine whether methods that use non-linear combination of miRNA expression values would improve predictive performances, the inventors evaluated quadratic discriminant analysis (QDA) and Support Vector Machines with a radial basis kernel (SVM-RBF). The inventors found that both approaches selected the same subset of miRNAs (miR-328, miR-222, miR-197 and miR-21) and both approaches had similar and improved performances: 85-86% accuracy, 86-87% sensitivity and 85-86% specificity. However, SVM-RBF had better performance on the training set (100% accuracy versus 93% for QDA); therefore, the inventors selected SVM-RBF as the best predictive model.

Model Validation using an Independent, In-Vivo Fine Needle Aspiration Sample Set The inventors then sought to validate prospectively the performance of the best predictive model (SVM-RBF) using the four selected miRNAs on an independent set of 72 in-vivo indeterminate thyroid lesions. Twenty-two lesions were malignant and 50 were benign on final histopathology. Normalized −ΔCTs are shown in FIG. 1 (Normalized −ΔCTs for the Derivation Group (A) and Validation Group (B) for each miRNA using a heatmap representation). Additionally, mean ΔCT values for all samples and each miRNA for the validation group are shown in Table 5. When applied to the −ΔCT for all four miRNAs the pre-trained SVM-RBF model correctly classified 65 out of 72 in-vivo Fine Needle Aspiration samples, with 100% sensitivity and 86% specificity for a diagnosis of cancer, for an overall accuracy of 90%. Five of the seven lesions that the model predicted incorrectly had a diagnosis of Hurthle cell neoplasm by fine needle aspiration sampling. Three were hyperplastic nodules with oncocytic features and 2 were follicular adenomas with oncocytic features on final pathology. When all 13 Hurthle cell neoplasms were excluded, the predictive performance of our model improved dramatically with 100% sensitivity, 95% specificity 97% overall accuracy in differentiating malignant from benign indeterminate lesions on FNA.

TABLE 5

Mean ΔCt in Validation group with two-tailed t-test p-values

|  | mir328 | mir222 | mir21 | mir197 |
| --- | --- | --- | --- | --- |
| Benign | −1.38 | −3.51 | −5.97 | −1.27 |
| Malignant | −3.12 | −7.62 | −8.61 | −3.11 |
| t-test (p-value) | <0.05 | <1e-7 | <0.001 | <0.05 |

Therefore, a method was developed to differentiate benign from malignant indeterminate thyroid lesions on 29 FNA samples using 4 miRNAs (miR-222, 328, 197, 21). This method was validated on an independent group of 72 indeterminate lesions, which accurately identified 100% of malignant and 86% of benign indeterminate fine needle aspiration lesion samples.

The following procedures and results demonstrate that the inventors have generated a predictive model to differentiate benign from malignant indeterminate thyroid lesions. Twenty-nine FNA samples were used for such development and the predictive model was validated on an independent group of 72 indeterminate lesions, which accurately identified 100% of malignant and 86% of benign indeterminate FNA lesions. Four miRNAs (miR-222, 328, 197, 21) were identified as being markers for malignant indeterminate thyroid lesions.

While selecting the most appropriate miRNAs for analysis, the foregoing results indicate that miRNA 146b and miRNA 181a were not useful for assessing the malignant/benign status of indeterminate thyroid lesions. When using the miR-222, 328, 197, and 21 microRNA panel most malignant pathologies present in indeterminate FNA lesions were properly characterized: mir-222 for CPTC and FVPTC, mir-328 and mir-197 FTC and mir-21 for FVPTC and FTC.

A model was therefore developed that is accurate for differentiating benign from malignant indeterminate lesions on FNA with a specificity of 86%. When Hurthle Cell Neoplasms were excluded the specificity improved to 95%. Without being bound to any particular theory or conclusion, Hurthle cell lesions may represent a separate entity with a different miRNA expression profile.

These data indicate that selected miRNA panel (miR-222, 328, 197, 21) is 100% sensitive for malignant pathology of indeterminate FNA lesions. Therefore, it would be reasonable to recommend a total thyroidectomy if malignancy is predicted. Furthermore, our model was also 95% predictive for benign pathology of indeterminate lesions when excluding Hurthle Cell lesions. Because the risk of a false negative result was only 5% in for indeterminate FNA lesions, a diagnostic hemithyroidectomy with its inherent risks and costs might be avoided in patients with benign lesions identified by the predictive model described herein.

This study is the largest reported to date on miRNA analysis of indeterminate thyroid FNA lesions. In summary, a predictive model was developed using four miRNAs (miR-222, 328, 197 and 21) that is 100% sensitive and 86% specific for differentiating malignant from benign indeterminate FNA thyroid lesions. When Hurthle cell neoplasms were excluded from the analysis our model had an improved specificity of 95% and an overall accuracy of 97% while retaining a sensitivity of 100% for malignant lesions.

REFERENCES

1. Hodgson N C, Button J, Solorzano C C. Thyroid cancer: is the incidence still increasing? Ann Surg Oncol 2004; 11:1093-7.
2. Cooper D S, Doherty G M, Haugen B R, Kloos R T, Lee S L, Mandel S J, et al. Management guidelines for patients with thyroid nodules and differentiated thyroid cancer. Thyroid 2006; 16:109-42.
3. Wang C, Crapo L M. The epidemiology of thyroid disease and implications for screening. Endocrinol Metab Clin North Am 1997; 26:189-218.
4. Faggiano A, Caillou B, Lacroix L, Talbot M, Filetti S, Bidart J M, et al. Functional characterization of human thyroid tissue with immunohistochemistry. Thyroid 2007; 17:203-11.
5. Mazzaferri E L. Thyroid cancer in thyroid nodules: finding a needle in the haystack. Am J Med 1992; 93:359-62.
6. Robertson M L, Steward D L, Gluckman J L, Welge J. Continuous laryngeal nerve integrity monitoring during thyroidectomy: does it reduce risk of injury? Otolaryngol Head Neck Surg 2004; 131:596-600.
7. Bartel D P. MicroRNAs: target recognition and regulatory functions. Cell 2009; 136:215-33.
8. Wiemer E A. The role of microRNAs in cancer: no small matter. Eur J Cancer 2007; 43:1529-44.
9. Gao Y, Wang C, Shan Z, Guan H, Mao J, Fan C, et al. miRNA expression in a human papillary thyroid carcinoma cell line varies with invasiveness. Endocr J 2010; 57:81-6.
10. Menon M P, Khan A. Micro-RNAs in thyroid neoplasms: molecular, diagnostic and therapeutic implications. J Clin Pathol 2009; 62:978-85.
11. Nikiforova M N, Chiosea S I, Nikiforov Y E. MicroRNA expression profiles in thyroid tumors. Endocr Pathol 2009; 20:85-91.
12. He H, Jazdzewski K, Li W, Liyanarachchi S, Nagy R, Volinia S, et al. The role of microRNA genes in papillary thyroid carcinoma. Proc Natl Acad Sci USA 2005; 102: 19075-80.
13. Pallante P, Visone R, Croce C M, Fusco A. Deregulation of microRNA expression in follicular-cell-derived human thyroid carcinomas. Endocr Relat Cancer 2010; 17:F91-104.
14. Sheu S Y, Grabellus F, Schwertheim S, Worm K, Broecker-Preuss M, Schmid K W. Differential miRNA expression profiles in variants of papillary thyroid carcinoma and encapsulated follicular thyroid tumours. Br J Cancer 2010; 102:376-82.

15. Chen Y T, Kitabayashi N, Zhou X K, Fahey T J, 3rd, Scognamiglio T. MicroRNA analysis as a potential diagnostic tool for papillary thyroid carcinoma. Mod Pathol 2008; 21:1139-46.
16. Nikiforova M N, Tseng G C, Steward D, Diorio D, Nikiforov Y E. MicroRNA expression profiling of thyroid tumors: biological significance and diagnostic utility. J Clin Endocrinol Metab 2008; 93:1600-8.
17. Pallante P, Visone R, Ferracin M, Ferraro A, Berlingieri M T, Troncone G, et al. MicroRNA deregulation in human thyroid papillary carcinomas. Endocr Relat Cancer 2006; 13:497-508.
18. Visone R, Russo L, Pallante P, De Martino I, Ferraro A, Leone V, et al. MicroRNAs (miR)-221 and miR-222, both overexpressed in human thyroid papillary carcinomas, regulate p27Kip1 protein levels and cell cycle. Endocr Relat Cancer 2007; 14:791-8.
19. Weber F, Teresi R E, Broelsch C E, Frilling A, Eng C. A limited set of human MicroRNA is deregulated in follicular thyroid carcinoma. J Clin Endocrinol Metab 2006; 91:3584-91.
20. Duda R. Pattern Classification. 2nd Edition ed: Willey-Interscience; 2000.
21. Venables W. Modern Applied Statistics with S (Statistics and Computing): Springer; 2010.
22. Gharib H. Changing trends in thyroid practice: understanding nodular thyroid disease. Endocr Pract 2004; 10:31-9.
23. Hegedus L. Clinical practice. The thyroid nodule. N Engl J Med 2004; 351:1764-71.
24. Layfield L J, Cibas E S, Baloch Z. Thyroid fine needle aspiration cytology: a review of the National Cancer Institute state of the science symposium. Cytopathology 2010; 21:75-85.
25. Nikiforov Y E, Steward D L, Robinson-Smith T M, Haugen B R, Klopper J P, Zhu Z, et al. Molecular testing for mutations in improving the fine-needle aspiration diagnosis of thyroid nodules. J Clin Endocrinol Metab 2009; 94:2092-8.
26. Xing M, Clark D, Guan H, Ji M, Dackiw A, Carson K A, et al. BRAF mutation testing of thyroid fine-needle aspiration biopsy specimens for preoperative risk stratification in papillary thyroid cancer. J Clin Oncol 2009; 27:2977-82.
27. Nikiforova M N, Nikiforov Y E. Molecular diagnostics and predictors in thyroid cancer. Thyroid 2009; 19:1351-61.
28. Eszlinger M, Paschke R. Molecular fine-needle aspiration biopsy diagnosis of thyroid nodules by tumor specific mutations and gene expression patterns. Mol Cell Endocrinol 2010; 322:29-37.
29. Sapio M R, Posca D, Raggioli A, Guerra A, Marotta V, Deandrea M, et al. Detection of RET/PTC, TRK and BRAF mutations in preoperative diagnosis of thyroid nodules with indeterminate cytological findings. Clin Endocrinol (Oxf) 2007; 66:678-83.
30. Zatelli M C, Trasforini G, Leoni S, Frigato G, Buratto M, Tagliati F, et al. BRAF V600E mutation analysis increases diagnostic accuracy for papillary thyroid carcinoma in fine-needle aspiration biopsies. Eur J Endocrinol 2009; 161:467-73.
31. Kebebew E, Peng M, Reiff E, Duh Q Y, Clark O H, McMillan A. ECM1 and TMPRSS4 are diagnostic markers of malignant thyroid neoplasms and improve the accuracy of fine needle aspiration biopsy. Ann Surg 2005; 242:353-61; discussion 61-3.
32. Kebebew E, Peng M, Reiff E, McMillan A. Diagnostic and extent of disease multigene assay for malignant thyroid neoplasms. Cancer 2006; 106:2592-7.
33. Barden C B, Shister K W, Zhu B, Guiter G, Greenblatt D Y, Zeiger M A, et al. Classification of follicular thyroid tumors by molecular signature: results of gene profiling. Clin Cancer Res 2003; 9:1792-800.
34. Prasad N B, Somervell H, Tufano R P, Dackiw A P, Marohn M R, Califano J A, et al. Identification of genes differentially expressed in benign versus malignant thyroid tumors. Clin Cancer Res 2008; 14:3327-37.
35. Finley D J, Lubitz C C, Wei C, Zhu B, Fahey T J, 3rd. Advancing the molecular diagnosis of thyroid nodules: defining benign lesions by molecular profiling. Thyroid 2005; 15:562-8.
36. Mazzanti C, Zeiger M A, Costouros N G, Umbricht C, Westra W H, Smith D, et al. Using gene expression profiling to differentiate benign versus malignant thyroid tumors. Cancer Res 2004; 64:2898-903.
37. Mazeh H, Mizrahi I, Halle D, Ilyayev N, Stojadinovic A, Trink B, et al. Development of a microRNA-based molecular assay for the detection of papillary thyroid carcinoma in aspiration biopsy samples. Thyroid 2011; 21:111-8.
38. Kitano M, Rahbari R, Patterson E E, Xiong Y, Prasad N B, Wang Y, et al. Expression profiling of difficult-to-diagnose thyroid histologic subtypes shows distinct expression profiles and identify candidate diagnostic microRNAs. Ann Surg Oncol 2011; 18:3443-52.
39. Frezzetti D, Menna M D, Zoppoli P, Guerra C, Ferraro A, Bello A M, et al. Upregulation of miR-21 by Ras in vivo and its role in tumor growth. Oncogene 2010.
40. Jazdzewski K, Boguslawska J, Jendrzejewski J, Liyanarachchi S, Pachucki J, Wardyn K A, et al. Thyroid Hormone Receptor {beta} (THRB) Is a Major Target Gene for MicroRNAs Deregulated in Papillary Thyroid Carcinoma (PTC). J Clin Endocrinol Metab 2010.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods, devices and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "an antibody" or "a nucleic acid" or "a polypeptide" includes a plurality of such antibodies, nucleic acids or polypeptides (for example, a solution of antibodies, nucleic acids or polypeptides or a series of antibody, nucleic acid or polypeptide preparations), and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The following statements of the invention are intended to describe some elements of the invention.

STATEMENTS OF THE INVENTION

1. A method of treating a patient comprising:
   a. determining whether a test dataset of expression levels is significantly within a malignant thyroid dataset or within a benign thyroid dataset to assess whether the test thyroid tissue sample is benign or malignant;
   b. treating the patient if the test thyroid tissue sample is assessed or determined to be malignant;
   wherein the test dataset of expression levels is a collection of quantified expression levels of mir-328, mir-222, mir-197, and mir-21 RNA in a test thyroid tissue sample from the patient;
   wherein the malignant thyroid dataset is a collection of quantified expression levels of mir-328, mir-222, mir-197, and mir-21 RNA from malignant thyroid tissue samples; and
   wherein the benign thyroid dataset is a collection of quantified expression levels of mir-328, mir-222, mir-197, and mir-21 RNA from benign, healthy, and/or non-cancerous thyroid tissue samples.

2. A method of avoiding unnecessary treatment of a patient comprising:
   a. determining whether a test dataset of expression levels is significantly within a malignant thyroid dataset or within a benign thyroid dataset to assess whether the test thyroid tissue sample is benign or malignant;
   b. avoiding unnecessary treatment of the patient if the test thyroid tissue sample is assessed or determined to be benign;
   wherein the test dataset of expression levels is a collection of quantified expression levels of mir-328, mir-222, mir-197, and mir-21 RNA in a test thyroid tissue sample from the patient;
   wherein the malignant thyroid dataset is a collection of quantified expression levels of mir-328, mir-222, mir-197, and mir-21 RNA from malignant thyroid tissue samples; and
   wherein the benign thyroid dataset is a collection of quantified expression levels of mir-328, mir-222, mir-197, and mir-21 RNA from benign, healthy, and/or non-cancerous thyroid tissue samples.

3. The method of statement 1 or 2, wherein the test thyroid tissue sample is obtained by fine needle aspiration.

4. The method of any of statements 1-3, further comprising obtaining the test thyroid tissue sample by fine needle aspiration.

5. The method of any of statements 1-4, wherein the test thyroid tissue sample is an indeterminate thyroid lesion tissue sample.

6. The method of any of statements 1-5, wherein the malignant thyroid dataset does not include quantified expression levels of mir-328, mir-222, mir-197, and/or mir-21 RNA from Hurthle Cell Lesions.

7. The method of any of statements 1-6, wherein the benign thyroid dataset does not include quantified expression levels of mir-328, mir-222, mir-197, and/or mir-21 RNA from Hurthle Cell Lesions.

8. The method of any of statements 1-7, further comprising obtaining or determining quantified expression levels of mir-328, mir-222, mir-197, and mir-21 RNA in the test thyroid tissue sample to generate the test dataset of expression levels.

9. The method of statement 8, wherein obtaining or determining quantified expression levels in the test thyroid tissue sample comprises polymerase chain reaction (PCR), reverse transcription, quantitative reverse-transcriptase-polymerase-chain-reaction (RT-PCR), serial analysis of gene expression (SAGE), next generation sequencing, gene expression microarray, northern blot analysis, in situ hybridization, or combinations thereof, to measure quantities of the microRNAs expression levels.

10. The method of any of statements 1-9, wherein determining whether the test dataset of expression levels is significantly within the malignant thyroid dataset or the benign thyroid dataset comprises use of a predictive algorithm.

11. The method of statement 10, wherein the predictive algorithm is a Support Vector Machine.

12. A method for constructing malignant/benign discrimination criteria for assessing test thyroid tissue samples suspected of being malignant comprising:

(a) training a benign/malignancy predictor, wherein the benign/malignancy predictor receives input comprising a malignant dataset and a benign dataset, and the predictor generates a multi-dimensional map distinguishing the malignant dataset from the benign dataset;
  (i) wherein the malignant dataset is a dataset of quantified microRNA expression levels obtained from thyroid tissue samples of patients having malignant thyroid cancer;
  (ii) wherein the benign dataset is a dataset of quantified microRNA expression levels obtained from thyroid tissue samples of patients without malignant thyroid cancer;
(b) optionally repeating step (a) for a plurality of iterations as data on at least one new quantified microRNA expression level is added to the malignant dataset or the benign dataset, to thereby construct malignant/benign discrimination criteria.

13. The method of statement 12, wherein the benign dataset is a dataset of quantified microRNA expression levels from thyroid tissue samples of patients having benign thyroid cancer.

14. The method of statement 12 or 13, wherein training a benign/malignancy predictor comprises use of an algorithm.

15. The method of statement 14, wherein the predictive algorithm is an algorithm comprising multidimensional evaluation for determining whether the at least one test sample expression level is statistically significantly within the malignant thyroid dataset or within the benign thyroid dataset to thereby assess whether the test thyroid tissue sample is benign or malignant.

16. The method of statement 14 or 15, wherein the algorithm is a Support Vector Machine.

17. The method of any of statements 12-16, further comprising step (c) comparing test result data comprising quantified microRNA expression levels obtained from a test thyroid tissue sample from a patient with the malignant dataset and the benign dataset to determine whether the test thyroid tissue sample is malignant or benign.

18. The method of statement 17, wherein the test thyroid tissue sample comprises an indeterminate thyroid lesion tissue.

19. The method of any of statements 12-18, wherein the quantified microRNA expression levels in the malignant dataset, the benign dataset and/or the test result data are expression levels of the following microRNAs: mir-328, mir-222, mir-197, mir-181a, mir-146b and/or mir-21 RNA.

20. The method of any of statements 12-19, wherein the quantified microRNA expression levels in the malignant dataset, the benign dataset and/or the test result data are expression levels of the following microRNAs: mir-328, mir-222, mir-197, and/or mir-21 RNA.

21. The method of any of statements 12-20, wherein the malignant thyroid dataset does not include quantified expression levels of mir-328, mir-222, mir-197, mir-181a, mir-146b and/or mir-21 RNA from Hurthle Cell Lesions.

22. The method of any of statements 12-21, wherein the benign thyroid dataset does not include quantified expression levels of mir-328, mir-222, mir-197, mir-181a, mir-146b and/or mir-21 RNA from Hurthle Cell Lesions.

23. The method of any of statements 12-22, wherein the quantified microRNA expression levels in the malignant dataset, the benign dataset and/or the test result data are determined by a procedure comprising polymerase chain reaction (PCR), reverse transcription, quantitative reverse-transcriptase-polymerase-chain-reaction (RT-PCR), serial analysis of gene expression (SAGE), next generation sequencing, gene expression microarray, northern blot analysis, in situ hybridization, or combinations thereof.

24. A method of assessing whether a test thyroid tissue sample is benign or malignant comprising:
  a. obtaining or determining a quantified expression level of at least one of the following microRNAs: mir-328, mir-222, mir-197, mir-181a, mir-146b and/or mir-21 RNA in the test thyroid tissue sample to obtain at least one test sample expression level;
  b. comparing the at least one test sample expression level to a malignant thyroid dataset and to a benign thyroid dataset;
  c. determining whether the at least one test sample expression level is statistically significantly within the malignant thyroid dataset or within the benign thyroid dataset to thereby assess whether the test thyroid tissue sample is benign or malignant;
  wherein the malignant thyroid dataset is a collection of quantified expression levels of mir-328, mir-222, mir-197, mir-181a, mir-146b and/or mir-21 RNA from malignant thyroid tissue samples; and
  wherein the benign thyroid dataset is a collection of quantified expression levels of mir-328, mir-222, mir-197, mir-181a, mir-146b and/or mir-21 RNA from benign, healthy, and/or non-cancerous thyroid tissue samples.

25. The method of statement 24, wherein the test thyroid tissue sample is obtained by fine needle aspiration.

26. The method of statement 24 or 25, further comprising obtaining the test thyroid tissue sample by fine needle aspiration.

27. The method of any of statements 24-26, wherein the test thyroid tissue sample is an indeterminate thyroid lesion tissue sample.

28. The method of any of statements 24-27, wherein the malignant thyroid dataset does not include quantified expression levels of mir-328, mir-222, mir-197, mir-181a, mir-146b and/or mir-21 RNA from Hurthle Cell Lesions.

29. The method of any of statements 24-28, wherein the benign thyroid dataset does not include quantified expression levels of mir-328, mir-222, mir-197, mir-181a, mir-146b and/or mir-21 RNA from Hurthle Cell Lesions.

30. The method of any of statements 24-29, wherein obtaining or determining a quantified expression level of at least one the microRNAs in the tissue sample comprises polymerase chain reaction (PCR), reverse transcription, quantitative reverse-transcriptase-polymerase-chain-reaction (RT-PCR), serial analysis of gene expression (SAGE), next generation sequencing, gene expression microarray, northern blot analysis, in situ hybridization, or combinations thereof, to measure quantities of the microRNAs expression levels.

31. The method of any of statements 24-30, wherein steps (b) and (c) are performed by a processor or computer.

32. The method of any of statements 24-31, wherein determining whether the at least one test sample expression level is significantly within the malignant thyroid dataset or the benign thyroid dataset comprises use of a predictive algorithm.

33. The method of statement 32, wherein the predictive algorithm is an algorithm comprising multidimensional evaluation for determining whether the at least one test sample expression level is statistically significantly within the malignant thyroid dataset or within the benign thyroid dataset to thereby assess whether the test thyroid tissue sample is benign or malignant.

34. The method of statement 32 or 33, wherein the predictive algorithm is a Support Vector Machine.

35. The method of any of statements 24-34, wherein quantified expression levels of at least two of the following microRNAs: mir-328, mir-222, mir-197, mir-181a, mir-146b and/or mir-21 RNA are obtained or determined.

36. The method of any of statements 24-35, wherein quantified expression levels of at least three of the following microRNAs: mir-328, mir-222, mir-197, mir-181a, mir-146b and/or mir-21 RNA are obtained or determined.

37. The method of any of statements 24-36, wherein quantified expression levels of at least four of the following microRNAs: mir-328, mir-222, mir-197, mir-181a, mir-146b and/or mir-21 RNA are obtained or determined.

38. The method of any of statements 24-37, wherein quantified expression levels of mir-328, mir-222, mir-197, and mir-21 RNA are obtained or determined.

39. The method of any of statements 24-38, further comprising treating a patient whose test thyroid tissue sample is assessed to be malignant.

40. The method of statement 39, wherein treating comprises performing surgery to remove malignant tissue or administering an anti-cancer agent.

41. A computer system comprising a processor, and a memory coupled to said processor and encoding one or more programs, wherein said one or more programs cause the processor to carry out at least one step of the method of any one of statements 1-40.

42. A computer program product comprising a device with a computer program mechanism encoded thereon, wherein the computer program mechanism may be loaded into the memory of a computer and cause the computer to carry out at least one step of the method of any one of statements 1-40.

43. The product of statement 42, wherein the device is a computer readable storage medium, a flash memory, a compact disc (CD), a digital versatile disc, digital video disc, or an article of manufacture that tangibly comprise a computer program and memory storage.

What is claimed:

1. A method of treating a patient comprising:
   a. determining a quantified expression level of mir-328, mir-222, mir-197, and mir-21 RNA in a test thyroid tissue sample from the patient to obtain a test dataset of expression levels;
   b. comparing the test dataset of expression levels of mir-328, mir-222, mir-197, and mir-21 to a malignant thyroid dataset and to a benign thyroid dataset;
   c. determining whether a test dataset of expression levels is significantly within a malignant thyroid dataset or within a benign thyroid dataset to assess whether the test thyroid tissue sample is benign or malignant; and
   d. treating the patient for malignant thyroid cancer if the test dataset of expression levels is significantly within a malignant thyroid dataset;

wherein the test dataset of expression levels comprises a collection of quantified expression levels of mir-328, mir-222, mir-197, and mir-21 RNA in a test thyroid tissue sample from the patient;
   wherein the malignant thyroid dataset comprises a collection of quantified expression levels of mir-328, mir-222, mir-197, and mir-21 RNA from malignant thyroid tissue samples; and
   wherein the benign thyroid dataset comprises a collection of quantified expression levels of mir-328, mir-222, mir-197, and mir-21 RNA from benign, healthy, and/or non-cancerous thyroid tissue samples.

2. The method of claim 1, wherein the test thyroid tissue sample is obtained by fine needle aspiration.

3. The method of claim 1, further comprising obtaining the test thyroid tissue sample by fine needle aspiration.

4. The method of claim 1, wherein the test thyroid tissue sample is an indeterminate thyroid lesion tissue sample.

5. The method of claim 1, wherein the malignant thyroid dataset or the benign thyroid dataset does not include quantified expression levels of mir-328, mir-222, mir-197, and/or mir-21 RNA from Hurthle Cell Lesions.

6. The method of claim 1, wherein determining quantified expression levels in the test thyroid tissue sample comprises polymerase chain reaction (PCR), reverse transcription, quantitative reverse-transcriptase-polymerase-chain-reaction (RT-PCR), serial analysis of gene expression (SAGE), next generation sequencing, gene expression microarray, northern blot analysis, in situ hybridization, or combinations thereof, to measure quantities of the microRNAs expression levels.

7. The method of claim 1, wherein the quantified expression levels are determined using next generation sequencing.

8. The method of claim 1, wherein steps (b) and (c) are performed by a processor or computer.

9. The method of claim 1, wherein determining whether the test dataset of expression levels is significantly within the malignant thyroid dataset or the benign thyroid dataset comprises use of a predictive algorithm.

10. The method of claim 9, wherein the predictive algorithm is a Support Vector Machine.

11. The method of claim 1, further comprising normalizing the quantified expression levels to an internal standard.

12. The method of claim 11, wherein the internal standard is a quantified RNA expression of RNU6B.

\* \* \* \* \*